US006800291B1

(12) United States Patent
Lipton et al.

(10) Patent No.: US 6,800,291 B1
(45) Date of Patent: *Oct. 5, 2004

(54) URO-GENITAL CONDITION TREATMENT SYSTEM

(75) Inventors: James M. Lipton, Woodland Hills, CA (US); Anna P. Catania, Milan (IT)

(73) Assignee: Zengen, Inc., Woodland Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/535,066

(22) Filed: Mar. 23, 2000

Related U.S. Application Data
(60) Provisional application No. 60/126,233, filed on Mar. 24, 1999.

(51) Int. Cl.$^7$ ........................ A61K 47/00; A61K 38/00; C07K 7/00

(52) U.S. Cl. ........................ 424/278.1; 514/2; 530/300

(58) Field of Search .......................... 514/18, 44, 14, 514/2, 15, 16; 424/184.1, 185.1, 278.1, 422, 430, 447, 426, 436; 530/300, 324, 326, 327, 328, 330, 331

(56) References Cited

U.S. PATENT DOCUMENTS

| | | | |
|---|---|---|---|
| 5,028,592 A | | 7/1991 | Lipton |
| 5,157,023 A | * | 10/1992 | Lipton .......................... 514/18 |
| 5,739,111 A | | 4/1998 | Mahe |
| 6,001,812 A | | 12/1999 | Mahe |
| 2002/0137685 A1 | * | 9/2002 | Catania et al. ................. 514/16 |
| 2002/0146374 A1 | * | 10/2002 | Lipton .......................... 424/50 |
| 2002/0183255 A1 | * | 12/2002 | Lipton et al. ................. 514/16 |

FOREIGN PATENT DOCUMENTS

| | | | |
|---|---|---|---|
| EP | 0972 522 A1 | | 1/2000 |
| FR | 2784028 | | 4/2000 |
| WO | WO 93/01211 | * | 1/1993 |
| WO | WO 97/10838 | * | 3/1997 |
| WO | WO/97/10838 | | 3/1997 |
| WO | WO/99/58101 | | 11/1999 |
| WO | PCT/US00/07846 | | 3/2000 |
| WO | WO00/42856 | | 7/2000 |

OTHER PUBLICATIONS

Wilma Barcellini, Letteria La Maestra, Giuliana Clerici, Letizia Garofalo, Anna T. Brini, James M. Lipton, Anna Catania, α–MSH Peptides Inhibit HIV–1 Expression in Chronically Infected Promonocytic U1 Cells and in Acutely Infected Monocytes, 12$^{th}$ World Aids Conference, Abstract 60685 (1998).
Getting, et al., POMC Gene–Derived Peptides Activate Melanocortin Type 3 Receptor on Murine Macrophages, Suppress Cytokine Release, and Inhibit Neutrophil Migration in Acute Experimental Inflammation, J. Immunol., vol. 162, No. 12, pp. 7446–7453, (1999).

Harris, et al., Alpha–melanocyte stimulating hormone (a–MSH) and melanin–concentrating hormone (MCH) stimulate phagocytosis by head kidney leucocytes of rainbow trout (*Oncorhynchus mykiss*) in vitro, Fish & Shellfish Immunol., vol. 8, 8:631–638 (1998).
Huang, et al., Role of central melanocortins in endotoxin–induced anorexia, Am. J. Physio (Regulatory, Integrative & Comparative Physiology, vol. 276, No. 3, pp. R864–R871 (1999).
Lipton, et al., Mechanisms of antiinflammatory action of the neuro immunomodulatory peptide alpha–MSH, Annals of the N.Y. Acad. Sci., vol. 840, pp. 373–380 (1998).
Weiss, et al., Corticotropin–peptide regulation of intracellular cyclic–AMP production in cortical neurons in primary culture, J. Neurochem. vol. 45, No. 3, pp. 869–874 (1985).
Airaghi, L., et. al., "Elevated concentrations of plasma α–MSH are associated with reduced disease progression in HIV–infected patients," J. Lab. Clin. Med. 133(3)309–315 (1999).
Airaghi L. Garofalo L. Cutuli MG. Delgado R. Carlin A. Demitri MT. Badalamenti S. Graziani G. Lipton JM. Catania A. Plasma concentrations of α–melanocyte–stimulating hormone are elevated in patients on chronic haemodialysis, Nephrolog Dialysis Transplantation 15:1212–1216, 2000.
Airaghi L, Lettino M, Manfredi MG, Lipton JM, Catania A. Endogenous cytokine antagonists during myocardial ischemia and thrombolytic therapy. Am. Heart J. 130:204–211, 1995.
Baker, et al., "Principles of Ambulatory Medicine," *Williams and Wilkins* (1982).
Barcellini, W., et al., "Inhibitory Influences of α–MSH peptides on HIV–1 expression in Monocytic cells," 12$^{th}$ World AIDS Conference Geneva, Abstract No. 60685, Jun. 28–Jul. 3, 1998.
Barcellini W, La Maestra L, Clerici G, Garofalo L, Brini AT, Lipton JM, Catania A. α–MSH peptides inhibit HIV–1 expression in chronically infected proonocytic U1 cells and in acutely infected monocytes. Journal of Leukocyte Biology 68:693–699, 2000.
Bickers, D., Sun–Induced Disorders, Emergency Medicine Clinics of North America, 3(4):659–663, 660 (1985.
Catania A, Airaghi L, Lipton JM. α–MSH in normal human physiology and disease states. Trends Endocrinol. Metab. 11:304–308, 2000.

(List continued on next page.)

*Primary Examiner*—James Housel
*Assistant Examiner*—Shanon Foley
(74) *Attorney, Agent, or Firm*—Michael J. Wise; Perkins Coie LLP

(57) ABSTRACT

The present invention is directed to a Lys-Pro-Val dimer, formulations containing the dimer and dimer applicators. The Lys-Pro-Val dimer is an effective anti-pyretic, anti-inflammatory and anti-microbial. The Lys-Pro-Val dimer is effective in treating fungal, bacterial and viral infections.

17 Claims, 15 Drawing Sheets

OTHER PUBLICATIONS

Catania A, Delgado R, Airaghi L, Cutuli M, Garafalo L, Carlin A, Demitri MT, Lipton JM. α–MSH in systemic inflammation: central and peripheral actions. Annals of the New York Academy of Sciences, 885:183–187, 1999.

Catania A, Grazia M, Manfredi MG, Airaghi L, Ceriani G, Gandino A, Lipton JM. Cytokine antagonists in infectious and inflammatory disorders. Annals of the New York Academy of Sciences 741: 149–161, 1994.

Catania A, Lipton JM,. α–melanocyte–stimulating hormone peptides in host response: from basic evidence to human research. Annals of the New York Academy of Sciences 680:412–423, 1993.

Catania A, Cutuli M, Garofalo L. Airaghi L, Valenza F, Lipton JM, Gattinoni L. Plasma concentrations and anti L–cytokine effects of α–melanocyte stimulating hormone in septic patients. Crit. Care Med. 28: 1403–1407, 2000.

Catania A, Airaghi L, Motta P, Manfredi MG, Annoni G, Pettenati C, Brambilla F and Lipton JM. Cytokine antagonists in aged subjects and their relation with cellular immunity. Journal of Gerontology: Biological Sciences 52A: B93–97, 1997.

Catania A, Manfredi MG, Airaghi L, Vivirito MC, Capetti A, Milazzo F, Lipton JM and Zanussi C. Plasma concentration of cytokine antagonists in patients with HIV infection. Neuroimmunomodulation 1: 42–49, 1994.

Catania A, Airaghi L, Manfredi MG, Vivirito MC, Milazzo F, Lipton JM, Zanussi C: Proopiomelanocortin–derived peptides and cytokines: relations in patients with acquired immunodeficiency syndrome: Clinical Immunology and Immunopathology 66: 73–79, 1993.

Cavello, J. and Deleo, V., Sunburn, *Dermatologic Clinics*, 4(2):181–187, (1986).

Ceriani G, Diaz J, Murphree S, Catania A, Lipton JM. The neuropeptide alpha–melanocyte–stimulating hormone inhibits experimental arthritis in rats. Neuroimmunomodulation 1:28–32, 1994.

Chiao H, Foster s, Thomas R, Lipton J, and Star RA. α–MSH reduces endotoxin–induced liver inflammation. J. Clin. Invest. 97:2038–2044, 1996.

Eberle, A.N., The Melanotrophins, *Karger, Basel, Switzerland* (1988).

Fitzpatrick, et al., Acute Effects of Ultraviolet Radiation on the Skin: The Sunburn Reaction, *Dermatology in General Medicine*, 4th Edition, 1651–1655, 1651 (1993).

Fitzpatrick, et al., "Color Atlas and Synopsis of Clinical Dermatology," (1983).

Foster, J. Sunburn, eMedicine—Online Medical Reference Textbook, (last modified may 1, 2000), <http://emedicine.com/emerg/topic798.htm.

Galimberti D, Baron PL, Meda L, Prat E, Scarpini E, Delgado R, Catania A, Lipton JM, Scarlato G. α–MSH peptides inhibit production of nitric oxide and tumor necrosis factorα by microglial cells activated with β–amyloid and interferon γ. Biochemical Biophysical Research Communications 263: 251–256, 1999.

"Harry's Comseticology", *Chemical Publishing*, 7$^{th}$ ed. (1982).

Huh S–K, Lipton JM and Batjer HH. The protective effects of α–melanocyte stimulating hormone on canine brainstem ischemia. Neurosurgery 40:132–139, 1997.

Ichiyama T, Sakai T, Catania A, Barsh GS, Furukawa A, Lipton JM. Systemically administered α–melanocyte–stimulating hormone peptides inhibit NF–κB activation in experimental brain inflammation. Brain Research 836: 31–37, 1999.

Ichiyama T, Zhao H, Catania A, Furukawa S, Lipton JM. α–melanocyte–stimulating hormone inhibits NF–κB activation and IαBκ degradation in human glioma cells and in experimental brain inflammation. Experimental Neurology 157:359–365, 1999.

Ichiyama T, Okada K, Campbell IL, Furukawa S, Lipton JM. NF–κB activation is inhibited in human pulmonary epithelial cells transfected with α–melanocyte–stimulating hormone vector. Peptides 21: 1473–1477, 2000.

Ichiyama T, Sakai T, Catania A, Barsh GS, Furukawa S, Lipton JM. Inhibitiono of peripheral NF–κB activation by central action of α–melanocyte–stimulating hormone. Journal of Neuroimmunology 99:211–217, 1999.

Lipton JM, Catania A, Ichiyama T. Marshalling the anti–inflammatory influence of the neuroimmunomodulator α–MSH. News Physiol. Sci, 15: 192–195.

Lipton JM, Catania A. The neuropeptide α–MSH: a modulator of host reactions. Seminars in Clinical Immunology 10:25–29, 1995.

Lipton JM, The Neuropeptide Alpha–Melanocyte–Stimulating Hormone Inhibits Experimental Arthritis in Rats, Neuroimmunomodulation 1:28–32 (1994).

Mayhall, Ten Home Remedies for Sunburn, *Seasonal Health*, (Jul. 14, 2000), <http://drkoop.com/wellness/seasonal/summer/sunburn.html>.

Potts, Sunlight, Sunburn, and Sunscreens, *Postgrad. med.*, 87:52–61 (1990).

Rajora N, Boccoli G, Catania A and Lipton JM. α–MSH modulates experimental inflammatory bowel disease. Peptides 18:381–385, 1997.

Remington's Pharmaceutical Sciences, *Mack Publishing Co.*, 18$^{th}$ ed. (1990).

Ryan, et al., "Inflammation," *a Scope Publication, The Upjohn Company*, (1977).

Taherzadeh S, Sharma S, Chhajlani V, Gantz I, Rajora N, Demitri MT, Kelly L, Zhao H, Catania A, Lipton JM. α–MSH and its receptors in regulation of tumor necrosis factor–α productin by human monocyte/macrophages. Am. J. Physiol. 276:R1289–R1294, 1999.

Watanabe, T, Hiltz ME, Catania A, Lipton JM. Inhibition of IL–1β–induced peripheral inflamation by peripheral and central administration of analogs of the neutropeptide α–MSH. Brain Research Bulletin 32:311–314, 1993.

Csata, M. et al., "Enhancement of *Candida albicans* killing activity of separated human epidermal cells by alpha–melanocyte stimulating hormone," British Journal of Dermatology, 121(1) 145–147 (1989).

*Robbins Pathologic Basis of Disease* 5$^{th}$ ed., Saunders Co., Philadelphia (1994) p. 335–337, 354–355, 1008, 1037–1038.

Lipton J.M., et al., "Anti–inflammatory Actions of the Neuroimmunomodulator α–MSH," *Immunol. Today* 18, 140–145 (1997).

Thody, A.J., et.al., "MSH Peptides are Present in Mammalian Skin," *Peptides* 4, 813–815 (1983).

Fox, J.A., et.al., "Immunoreactive α–Melanocyte Stimulating Hormone, Its Distribution in the Gastrintestinal Tract of Intact and Hypophysectomized Rats," *Life Sci.* 18, 2127–2132 (1981).

Catania, A., et. al., "α–Melanocyte Stimulating Hormone in the Modulation of Host Reactions," *Endocr. Rev.* 14, 564–576 (1993).

Catania, A., et al., "Melanocortin Peptides Inhibit Production of Proinflammatory of Cytokines in Blood of HIV–Infected Patients," *Peptides*, 19(6):1099–1104 (1998).

Cutull, M. et. al., "Antimicrobial effects of α–MSH peptides," Journal of Leukocyte Biology 67:233–239 (2000).

Rajora, N., et. al., "α–MSH Production Receptors and Influence on Neopterin, in a Human Monocyte/macrophage Cell Line," *J. Leukoc. Biol.* 59, 248–253 (1996).

Star, R.A., et al., "Evidence of Autocrine Modulation of Macrophage Nitric Oxide Synthase by α–MSH," *Proc. Nat'l. Acad. Sci.* (*USA*) 92, 8015–8020 (1995).

Lipton, J.M., et al., "Anti–inflammatory Effects of the Neuropeptide α–MSH in Acute Chronic and Systemic inflammation," *Ann. N.Y. Acad. Sci.* 741, 137–148 (1994).

Rajora, N., et al., "α–MSH Modulates Local and Circulating tumor Necrosis Factor α in Experimental Brain Inflammation," *J. Neuroosci*, 17, 2181–2186 (1995).

Richards, D.B., et. al., "Effect of a–MSH (11–13) (lysine–proline–valine) on Fever in the Rabbit," *Peptides* 5, 815–817 (1984).

Hiltz, M. E., et. al., "Anti–inflammatory Activity of a COOH–terminal Fragment of the Neuropeptide α–MSH," *FASEB J.* 3, 2282–2284 (1989).

Gow, N.A., "Germ Tube Growth of *Candida albicans*," *Curr. Topics Med. Myco.* 8, 43–55 (1997).

Stevens, D.L., "Could Nonsteroidal Anti–inflammatory Drugs (NSAIDs) Enhance Progression of Bacterial Infections to Toxic Shock Syndrome?," *Clin. Infect. Dis.* 21, 977–80 (1997).

Capsoni, F., et. al., "Effect of Corticosteroids on Neutrophil Function: Inhibition of Antibody–dependent Cell–Mediated Cytotoxicity (ADCC)," *J. Immunopharmacol.* 5, 217–30 (1983).

Bhattacharya A., et. al., "Effect of Cyclic AMP on RNA and Protein Synthesis in *Candida albicans*," *Biochem, Biophysics. Res. Commun.*, 77: 1483–44 (1977).

Baker, M., et. al., "The Relationship between Interleukin–6 and Herpes Simplex Virus Type–1: Implications for Behavior and Immunopathology," *Brain Behav. Immun.* 13(3):201–11 (1999).

Noisakran S., e al., "Lymphocytes Delay Kinetics of HSV–1 Reactivation from in vitro Explants of Latent Infected Trigeminal Ganglia," *J. Neuroimmunol.* 95(1–2):1260–35 (1999).

Walev, I., et.al., "Enhancement of TNF–alpha of Reactivation and Replication of Latent Herpes Simplex Virus from Trigeminal Ganglia of Mice," *Arch Virol.* 140(6):987–92 (1995).

Domk–Optiz, I., et. al., "Stimulation of Macrophages by Endotoxin Results in the Reactivation of a Persistent Herpes Simplex Virus Infection," *Scand J. Immunol.* 32(2):69–75 (1990).

Fauci, A.S., "Host Factors in the Pathogenesis of HIV–induced Disease," *Nature* 384: 529 (1996).

Patel, A., et. al., "Herpes Simplex Type 1 Induction of Persistent NF–κB Nuclear Translocation Increases the Efficiency of Virus Replication," *Virology* 247(2):212–22 (1998).

Holdeman, M., et. al., "Antipyretic Activity of a Potent α–MSH Analog," *Peptides* 6, 273–5 (1985).

Deeter, L.B., et. al., "Antipyretic Properties of Centrally Administered α–MSH Fragments in the Rabbit," *Peptides*, 9, 1285–1288 (1989).

Hiltz, M.E., "Anti–Inflammatory Activity of α–MSH (11–13) Analogs: Influences of Alterations in Stereochemistry," *Peptides* 12, 767–71 (1991).

Lipton, J.M., "Neuropeptide α–Melanocyte–Stimulating Hormone in Control of Fever, the Acute Phase Response, and Inflammation," *Neuroimmune Networks: Physiology and Diseases*, (Alan R. Liss, Inc. 1989) pp. 243–250.

Hiltz, M.E., et. al., "Alpha–MSH Peptides Inhibit Acute Inflammation and Contact Sensitivity," *Peptides*, 11:979–982 (1990).

Uehara, Y., et. al., "Carboxyl–terminal tripeptide of α–Melanocyte–Stimulating Hormone anagonizes interleukin–1–induced anorexia," *European Journal of Pharmacology*, 220: 110–122 (1992).

Mugridge, K.G., et. al., "α–Melanocyte–Stimulating Hormone reduces interleukin–1β effects on rat stomach preparations possibly through interference with type 1 receptor," *European Journal of Pharmacology*, 197: 151–155 (1991).

Hiltz, M.E., et. al., "α–MSH Peptides Inhibit Acute Inflammation Induced in Mice by rIL–1β, RIL–6, rTNF–α and endogenous pyrogen but not that cause by LTB4, PAF and rIL–8," *Cytokine* 4(4):320–328 (1992).

Macaluso, A., et al., "Antiinflammatory Influences of α–MSH molecules: Central Neurogenic and Peripheral Actions," *The Journal of Neuroscience*, 14(4):2377–2382 (1994).

Lyson, K., et. al., "Binding of Anti–Inflammatory α–Melanocyte–Stimulating Hormone Peptides and Proinflammatory Cytokines to Receptors on Melanoma Cells," *Neuroimmunomodulation*, 1:121–126 (1994).

Ceriani, G., et. al., "Central Neurogenic Antiinflammatory Action of α–MSH: Modulation of Peripheral Inflammation Induced by Cytokines and other Mediators of Inflammation," *Neuroendocrinology*, 59:138–143 (1994).

Wong, K.Y., et. al., "A Potential Mechanism of Local Anti–inflammatory Action of Alpha–Melanocyte–Stimulating Hormone within the Brain: Modulation of Tumor Necrosis Factor–Alpha Production by Human Astrocytic Cells," *Neuroimmunomodulation*, 4:37–41 (1997).

Delgado, R., et. al., "Melanocortin peptides inhibit production of proinflammatory cytokines and nitric oxide by activated microglia," *Journal of Leukocyte Biology*, 63: 740–745 (1998).

Szalay, K.S., et. al., "Structure–activity studies with ACTH/α–MSH fragments on corticosteroid secretion of isolated zona glomerulosa and fasciculata cells," *Regulatory Peptides*, 11: 187–192 (1985).

Lichtensteiger, W., and Monnet, F., "Differential Response of Dopamine Neurons to α–Melanotropin and Analogues in Relation to Their Endocrine and Behavioral Potency," *Life Sci.* 25:2079–2087 (1979).

Eberle, A. and Schwyzer, R., Hormone Receptor Interactions, *Clinical Endocrinology* 5, Suppl. 41s–48s (1976).

Lipton, J.M., Modulation of Host Defense by the Neuropeptide α–MSH, *The Yale Journal of Biology and Medicine* 63: 173–182 (1990).

Hart, D.A., et. al., "*Staphylococcus Aureus* Strains Differ in Their in Vitro Responsiveness to Human Urokinase: Evidence that Methicillin–Resistant Strains are Predominantly Nonresponsive to the Growth–Enhancing Effects of Urokinase," *Can. J. Microbiol.* 42: 1024–31 (1966).

Catania, A., et. al., "The Neuropeptide α–MSH in HIV Infection and Other Conditions in Humans," *Ann. N.Y. Acad. Sci.* 840:848–856 (1998).

Wenzel, R.P. and Pfaller, M.A., "Candida Species: Emerging Hospital Bloodstream Pathogens," *Infect. Control. Hosp. Epidemiol.* 12: 523–4 (1991).

Cartledge, J.D., et. al., "Clinically Significant Azole Cross–Resistance in Candida Isolates from HIV–Positve Patients with Oral Candidosis," *AIDS* 11:1839–44 (1997).

Catania, A.; et. al., "The Neuropeptide α–MSH has Specific Receptors on Neutrophils and Reduces Chemotaxis in Vitro," *Peptides*17, 675–679 (1996).

Luger, T.A., et. al., "Production of Immunosuppressing Melanotropins by Human Keratinocytes," *Ann. N.Y. Acad. Sci.* 680: 567–570 (1993).

van Nispen, J.W. and Greven, H.M., "Structure–Activity Relationships of Peptides Derived From ACTH, β–LPH and MSH With Regard To Avoidance Behavior in Rats," *Pharmac. Ther.* 16:67–102 (1982).

"Vaginitis," National Institute of Child Health and Human Development—Publication On–line (last modified Jan. 12, 2000).<www.nichd.nih.gov/publications/pubs/vagtoc.html>.

"Tampons and Asbestos, Dioxins, & Toxic Shock Syndrome," FDA Center for Devices and Radiological Health (Jul. 23, 1999), <http://www.fda.gov/cdrh/ocd/tamponsabs.html>.

Khurshid, M.A., et. al., "*Staphylococcus aureus* with Reduced Susceptibility to Vancomycin—Illinois, 1999," *Morbidity and Mortality Weekly Report*, 48(51): 1165–1167 (2000), <http://www.cdc.gov/epo/mmwr/preview/mmwrhtml/mm4851a1.htm>.

"Women's Health, Urinary Tract Infections: A Patient's Guide to Treatment," *AMA Health Insight, On–Line Health Information for Everyone* (last updated Oct. 30, 1998) <http://www.ama–assn.org/insight/h focus/wom hlth/uti/uti.htm>.

Fauchere et al. FEBS. 1985; 183 (2):283–286.*

Fauchere et al. Helvetica Chemica Acta. 1985; 68: 770–776.*

Feuilloley et al. Journal of Steroid Chemistry. 1990; 35(5):583–592.*

Loetscher et al. Journal of Biological Chemistry.Aug., 1998; 273(35):22279–22283.*

Rajora et al. Peptides. 1997; 18(3): 381–385.*

* cited by examiner

Influence of α-MSH peptides on *C. albicans* germ tube formation.
A) blastospores;
B) horse serum-induced germ tube formation;
C) effect of α-MSH (1-13) treatement on germ tube formation
D) effect of α-MSH (11-3) treatement on germ tube formation

SEQUENCE LISTING

```
<160> NUMBER OF SEQ ID NOS: 10

<210> SEQ ID NO 1
<211> LENGTH: 3
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties.

<400> SEQUENCE: 1

Lys Pro Val
1

<210> SEQ ID NO 2
<211> LENGTH: 7
```

```
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties.

<400> SEQUENCE: 2

Met Glu His Phe Arg Trp Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties.

<400> SEQUENCE: 3

His Phe Arg Trp Gly Lys Pro Val
1               5

<210> SEQ ID NO 4
<211> LENGTH: 13
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties.

<400> SEQUENCE: 4

Ser Tyr Ser Met Glu His Phe Arg Trp Gly Lys Pro Val
1               5                   10

<210> SEQ ID NO 5
<211> LENGTH: 4
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties.

<400> SEQUENCE: 5

Gly Lys Pro Val
1

<210> SEQ ID NO 6
<211> LENGTH: 5
<212> TYPE: PRT
<213> ORGANISM: Artificial Sequence
<220> FEATURE:
<223> OTHER INFORMATION: C-terminal sequences of alpha-MSH

<400> SEQUENCE: 6

Trp Gly Lys Pro Val
1               5

<210> SEQ ID NO 7
<211> LENGTH: 6
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties.

<400> SEQUENCE: 7

Arg Trp Gly Lys Pro Val
1               5
```

```
<210> SEQ ID NO 8
<211> LENGTH: 4
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties.

<400> SEQUENCE: 8

Cys Lys Pro Val
1

<210> SEQ ID NO 9
<211> LENGTH: 35
<212> TYPE: DNA
<213> ORGANISM: Artificial Sequence
<220> FEATURE:
<223> OTHER INFORMATION: Oligonucleotide probes for NF-kB.

<400> SEQUENCE: 9 gat cca agg gga ctt tcc gct ggg gac ttt cca tg                          35

<210> SEQ ID NO 10
<211> LENGTH: 35
<212> TYPE: DNA
<213> ORGANISM: Artificial Sequence
<220> FEATURE:
<223> OTHER INFORMATION: Oligonucleotide probes for NF-kB.

<400> SEQUENCE: 10 gat cca tgg aaa gtc ccc agc gga aac tcc cct tg                          35
```

URO-GENITAL CONDITION TREATMENT SYSTEM

PRIORITY CLAIM

The present application is a utility application that claims priority to U.S. Provisional Patent Application Ser. No. 60/126,233 entitled Antimicrobial Amino-Acid Sequences Derived from Alpha-Melanocyte Stimulating Hormone, filed Mar. 24, 1999.

FIELD OF THE INVENTION

The present invention relates to the field of treatment for uro-genital conditions.

BACKGROUND OF THE INVENTION

Uro-genital conditions or diseases commonly affect both men and women. These conditions include infections and/or inflammation of the urinary system and the genital system. For example, according to the National Institute of Child Health and Human Development (NICHD), most women will have at least one form of vaginitis in their lifetime. The causes for vaginitis range from bacterial, fungal, or viral infections to irritations from chemicals in creams, sprays, or even clothing that are in contact with this area. For women with bacterial and fungal infections, these infectious agents often originate from the rectal area and migrate across the perineum to reach the vagina or the urethra.

A common type of vaginitis is candidiasis or yeast infection that is most commonly caused by *Candida albicans*. The Candida species are part of an individual's normal flora of microbial organisms present in skin, mouth, and the gastrointestinal tract. They also live in small number in a woman's vagina. They grow best in warm, moist surfaces such as the vagina or the oral cavity. They are normally non-pathogenic, but when a change in their environment occurs, such as in response to a woman's hormonal changes in menopause, pregnancy, or in response to stress, they can overgrow to cause a yeast infection. These changes can also occur in immunosuppressed or compromised individuals such as people undergoing chemotherapy, taking immunosuppresants, or afflicted with-AIDS.

Current treatment for candidiasis includes over the counter drugs with active ingredients such as butoconazole nitrate (Femstat®), clotrimazole (Gyne-Lotrimin® and others), miconazole (Monistate® and others), and tioconazole (Vagistat®). These drugs are topically applied in the vagina and break down Candida's cell wall. Other similar treatments include prescription drugs with active ingredients in the same family such as fluconazole (Diflucan®), terconazole (Terazol®), and ketoconazole (Nizoral®).

Although vaginitis has been commonly associated with Candida, bacterial vaginosis is actually the most common vaginal infection in women of reproductive age according to the NICHD. Overgrowing of bacteria in the vagina causes bacterial vaginosis much like Candida, but the drugs used for its treatment are different.

On the other hand, men can also contract Candida infections on their penis involving the glans and the prepuce. Balanoposthitis, a nonspecific infection of the glans and prepuce, is caused by a wide variety of organisms including fungi such as Candida and pyogenic bacteria such as staphylococci.

Staphylococci are gram positive bacteria that are normally present in skin and other mucosal membranes of the body. *Staphylococcus aureus*, in particular, is a virulent pathogen that causes a myriad of conditions and diseases stemming from skin lesions, endocarditis, respiratory infection, food poisoning, to toxic shock syndrome. For women using highly absorbent tampons, it is known that *S. aureus* can colonize the vagina and secrete a toxin called toxic shock syndrome toxin (TSST-1). According to the Food and Drug Administration, approximately half of the toxic shock syndrome cases reported today are associated with tampon use during menstruation and usually in young women.

*S. aureus* infections are commonly treated with methicillin. Although it is very effective, some strains of *S. aureus* have developed resistance to methicillin, and only a few antibiotics can successfully treat these methicillin-resistant *Staphylococcus aureus* (MRSA). One of these antibiotics commonly used for MRSA is vancomycin. A strain of *S. aureus*, however, with reduced susceptibility to vancomycin (VISA) has already been identified. The emergence of antibiotic resistant bacterial strains has created a need for alternative ways to combat bacterial infections.

In addition to infection by fungi and bacteria, viral vaginitis is also common. These infections are most often transmitted through sexual intercourse. Viral vaginitis includes infection by herpes simplex virus (HSV) or human papillomavirus (HPV). HSV viruses, for example, replicate in the genital area, which is the site of entrance, and also infect the neurons that innervate the genitals. To avoid the body's immune system, HSV viruses can remain latent in these neurons, and become reactivated in response to environmental conditions such as stress, immunosuppression, irradiation, or viral infection. Current treatments for HSV include drugs such as acyclovir, famciclovir, or valacyclovir.

As for the urinary system, according to the American Medical Association, urinary tract infections (UTIs) are one of the most common disorders prompting a physician visit. These infections are most often caused by *Escherichia coli*, but can also involve organisms such as Candida and Staphylococci. These infections can start at the urethra and travel up to the bladder causing cystitis. Ultimately, it can even ascend to the kidneys through the ureters and cause pyelonephritis. Both men's and women's urinary systems can become infected with these microorganisms.

Since uro-genital conditions are not confined to one single cause, current treatments require different drugs to treat specific causes. These causes have to be first identified. Identification requires time, but more so, requires a gynecological examination for women to determine the specific infectious agents or lack thereof.

With the increased use of antibiotics and other drugs, microorganisms, such as methicillin-resistant staphylococcus aureus, are increasingly developing resistance to currently available drugs. Thus, a continuing need exists for new classes of drugs that can combat the broad spectrum of infectious agents.

SUMMARY OF THE INVENTION

The present invention is directed to a system for treating uro-genital conditions. One aspect of this invention involves the treatment system comprising one or more polypeptides with a amino acid sequence including KPV (SEQ. ID. NO. 1), MEHFRWG (SEQ. ID. NO. 2), HFRWGKPV (SEQ. ID. NO. 3), or SYSMEHFRWGKPV (SEQ. ID. NO. 4) for treatment of uro-genital conditions. The one or more polypeptides can also be a dimer formed from any of the amino acid sequence above. Uro-genital conditions can include infections, inflammation, or both. In one preferred embodiment of the invention, the uro-genital condition includes infection and/or inflammation of the vagina, vulva, urinary tract, penis, and/or the rectum. In another preferred embodiment of the invention, the one or more polypeptides are dissolved in a carrier. In another preferred embodiment of the invention, the one or more polypeptides are associated with a tampon for preventing toxic shock syndrome. In another preferred embodiment, the one or more polypeptides are associated with a contraceptive for prevention of sexually transmitted diseases or infections. In another preferred embodiment, the one or more polypeptides are associated with a suppository for insertion into the vagina or rectum. In another preferred embodiment of the invention, the one or more polypeptides are dissolved in a liquid carrier for douching the vagina.

GENERAL DESCRIPTION OF THE INVENTION

Figure 1:
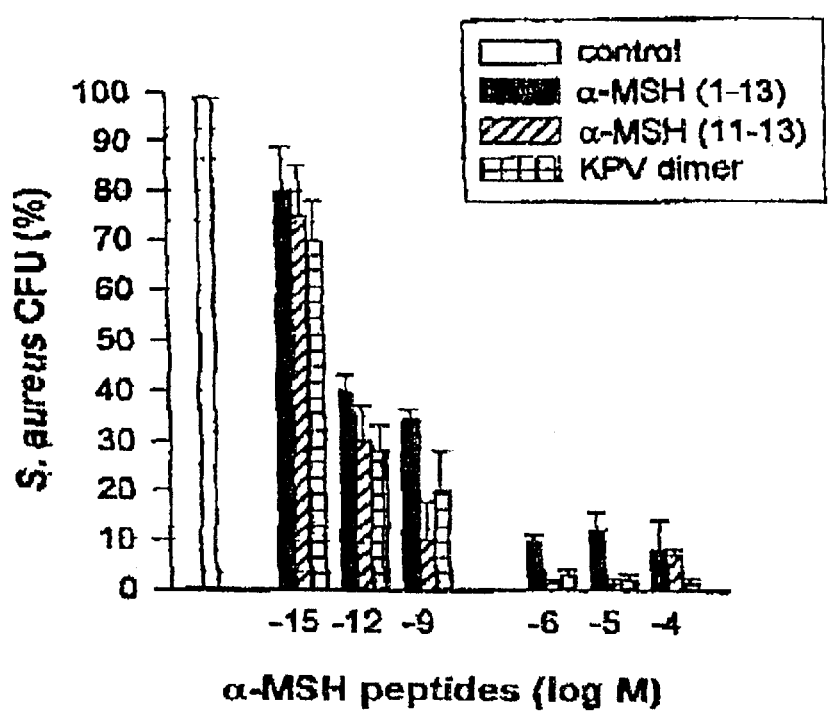
FIG. 1 shows the inhibitory effects of α-MSH and/or its derivatives on the growth of *S. aureus*.

The references cited below are hereby incorporated by reference as if fully set forth herein. The present invention involves a method and system for treating uro-genital conditions with the use of alpha-melanocyte stimulating hormone ("α-MSH") and/or its derivatives. α-MSH is an ancient thirteen amino-acid peptide (SEQ. ID. NO. 4) produced by post-translational processing of the larger precursor molecule propiomelanocortin. It shares the 1–13 amino acid sequence with adrenocorticotropic hormone ("ACTH"), also derived from propiomelanocortin. α-MSH is known to be secreted by many cell types including pituitary cells, monocytes, melanocytes, and keratinocytes. It can be found in the skin of rats, in the human epidermis, or in the mucosal barrier of the gastrointestinal tract in intact and hypophysectomized rats. See e.g. Eberie, A. N., *The Melanotrophins*, Karger, Basel, Switzerland (1998); Lipton, J. M., et. al., *Anti-inflammatory Influence of the Neuroimmunomodulator α-MSH, Immunol. Today* 18, 140–145 (1997); Thody, A. J., et.al., *MSH Peptides are Present in Mammalian Skin, Peptides* 4, 813–815 (1983); Fox, J. A., et.al., *Immunoreactive α-Melanocyte Stimulating Hormone, Its Distribution in the Gastrointestinal Tract of Intact and Hypophysectomized Rats, Life. Sci.* 18, 2127–2132 (1981).

α-MSH and its derivatives are known to have potent antipyretic and anti-inflammatory properties, yet they have extremely low toxicity. They can reduce production of host cells' proinflammatory mediators in vitro, and can also reduce production of local and systemic reactions in animal models for inflammation. The "core" α-MSH sequence (4–10) (SEQ. ID. NO. 2), for example, has learning and memory behavioral effects but little antipyretic and anti-inflammatory activity. In contrast, the active message sequence for the antipyretic and anti-inflammatory activities resides in the C-terminal amino-acid sequence of α-MSH, that is, lysine-proline-valine ("Lys-Pro-Val": or "KPV") (SEQ. ID. NO. 1). This tripeptide has activities in vitro and in vivo that parallel those of the parent molecule. The anti-inflammatory activity of α-MSH and/or its derivatives are disclosed in the following two patents and are hereby incorporated by reference: U.S. Pat. No. 5,028,592, issued on Jul. 2, 1991 to Lipton, J. M., entitled Antipyretic and Anti-inflammatory Lys Pro Val Compositions and Method of Use; U.S. Pat. No. 5,157,023, issued on Oct. 20, 1992 to Lipton, J. M., entitled Antipreytic and Anti-inflammatory Lys Pro Val Compositions and Method of Use; see also Catania, A., et. al., α-*Melanocyte Stimulating Hormnone in the Modulation of Host Reactions, Endocr. Rev.* 14, 564–576 (1993); Lipton, J. M., et.al., *Anti-inflammatory Influence of the Neuroimnunomodulator of α-MSH, Immunol. Today* 18, 140–145 (1997); Rajora, N., et. al., α-*MSH Production Receptors and Influence on Neopterin, in a Human Monocyte/macrophage Cell Line, J. Leukoc. Biol.* 59, 248–253 (1996); Star, R. A., et. al., *Evidence of Autocrine Modulation of Macrophape Nitric Oxide Synthase by* α-*MSH, Proc. Nat'l. Acad. Sci. (USA)* 92, 8015–8020 (1995); Lipton, J. M., et.al., *Anti-inflammatory Effects of the Neuropeptide* α-*MSH in Acute Chronic and Systemic inflammation, Ann. N.Y. Acad. Sci.* 741, 137–148 (1994); Fajora, N., et.al., α-*MSH Modulates Local and Circulating tumor Necrosis Factor α in Experimental Brain Inflammation, J. Neuroosci,* 17, 2181–2186 (1995); Richards, D. B., et. al., *Effect of* α-*MSH* (11–13) (*lysine-proline-valine*) *on Fever in the Rabbit, Peptides* 5, 815–817 (1984); Hiltz, M. E., et. al., *Anti-inflammatory Activity of a COOH-terminal Fragment of the Neuropeptide* α-*MSH, FASEB J.* 3, 2282–2284 (1989).

In addition to its anti-inflammatory and anti-pyretic function, one aspect of the present invention involves the anti-microbial or anti-infection activity of α-MSH and/or its derivatives. As described below, α-MSH and/or its derivatives have significant anti-infection uses, including, for example, use in reducing the viability of microbes, reducing the germination of yeast, killing microbes without reducing the killing of microbes by human neutrophils, for treating inflammation associated with microbial infection without reducing microbial killing, increasing the accumulation of cAMP in microbes, and inhibiting the replication and expression of viral pathogens.

In a preferred embodiment of the invention, these anti-microbial or anti-infection activities are most particularly associated with the C-terminal amino-acid sequence—KPV. This tripeptide, along with α-MSH and its derivatives, are effective over a very broad range of concentrations, including picomolar concentrations that normally occur in human plasma.

As discussed in the background section, uro-genital conditions are not confined to one single cause. Multiple organisms and infectious agents, from bacteria, fungi, to viruses, individually or in combination can cause a wide variety of conditions including vaginitis, vulvitis, urethritis, balanophosthithis, candidiasis, sexually transmitted diseases, and toxic shock syndrome. For treatment of these conditions, α-MSH and/or its derivatives can be applied locally to the site of the infection and/or inflammation by methods known in the art. For example, α-MSH and its derivatives can be dissolved in solutions such as phosphate buffer saline, hyalurinate, methylcellulose, carboxymethlcellulose, or ethanol. Common carriers such as ointment, cream, gel, dissolvable pill, aerosol spray, suppository, liquid solution for douche, or the absorbent material of tampons can carry α-MSH and/or its derivatives as active ingredients for treating uro-genital conditions. These carriers can be applied to the site of the infection or inflammation by an applicator such as syringes or syringe-like apparati, bandages, catheters, tubes with a plunger, spatula or other types of flat surface applicators, condoms, sponges, diaphragms, tampon applicators, or fingers.

More specifically, the preferred embodiment of the invention is to dissolve α-MSH and/or its derivatives in a liquid-based carrier. This carrier carrying the solvated α-MSH and/or its derivatives is then stored in a pressurized canister. Upon release of the carrier by a release valve or other mechanisms from the pressurized canister, an aerosol foam is formed and captured into a syringe or a syringe-type apparatus. The syringe is then partially inserted into the vagina and its contents delivered into the vaginal canal. The syringe or syringe-type apparatus and its opening can also be molded to different size, shapes, and lengths to accommodate insertion into different uro-genital areas such as the urethra or the rectum.

Another preferred embodiment of the invention is a suppository that comprises a carrier. This carrier such as a gel or glycerin is solid or semi-solid at room temperature, but melts at body temperature when inserted into the vagina or rectum. This carrier carrying the solvated α-MSH and/or its derivatives are delivered into the site of uro-genital condition when the carrier melts.

Delivering α-MSH and its derivatives to the outside area of the uro-genital area such as the vulva or the glans and prepuce of the penis can be achieved by topically applying a cream, ointment, gel, spray, foam, or balm, the compositions of which are already well known in the art.

In another aspect of the invention, tampons can be treated with α-MSH and/or its derivatives during the manufacturing process. The presence of α-MSH in tampons may inhibit the growth of microorganisms such as *Staphylococcus aureus* that secretes the toxic shock syndrome toxin (TSST-1). The processes for making tampons are already well known in the art. Treatment of the tampon's absorbent material with α-MSH or its derivatives may be accomplished by first soaking the absorbent material in a solution of α-MSH and/or its derivatives. The absorbent material can then be allowed to dry. Alternatively, α-MSH may be sprinkled onto the tampon's absorbent material as dry powder.

In another aspect of the invention, α-MSH and/or its derivatives may be delivered to the site of the infection by using contraceptives such as condoms, diaphragms, sponges, or other barrier-type mechanisms used for preventing pregnancy or sexually transmitted diseases. α-MSH and/or its derivatives can be dissolved in the lubricant used in condoms, in the gel or foam used together with the diaphragms, or in any other spermicidal solution used in conjunction with condoms, diaphragms, or sponges.

In another aspect of the invention, α-MSH and/or its derivatives may be dissolved in a liquid for use with a douche. The liquid can be delivered by the douche into the vagina for treating infection and/or inflammation.

The following examples demonstrate the ability and application of α-MSH and its derivatives to combat infection. Methods in microbiology, molecular biology, and cell culture used but not explicitly described in this disclosure have already been amply reported in the scientific literature. These methods are well within the ability of one skilled in the art.

Figure 16:
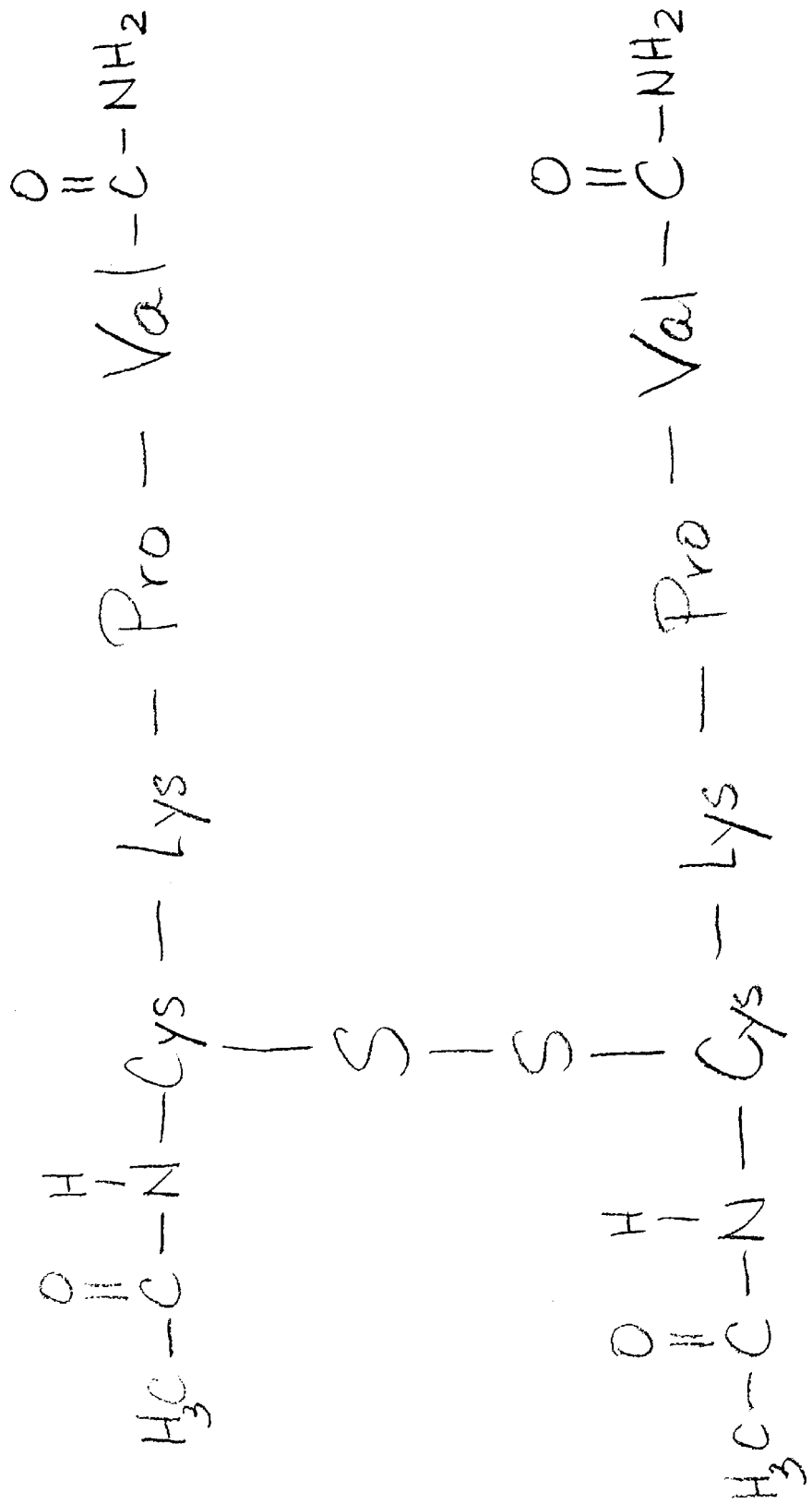
FIG. 16 shows a representation of the chemical structure of one form of the KPV dimer for use with one aspect of the invention.

The peptides used in the following examples include: α-MSH (1–13) (SEQ. ID. NO. 4), (4–10) (SEQ. ID. 002), (6–13) (SEQ. ID. 003), and (11–13) (SEQ. ID. NO. 1), all of which N-acetylated and C-amidated, and ACTH (1–39) and (18–39) (CLIP). These peptides were prepared by solid-phase peptide synthesis and purified by reversed phased high performance liquid chromatography. Some examples also include a dimer of the amino acid sequence CKPV (SEQ. ID. NO. 8), which also was N-acetylated and C-amidated (the "KPV dimer"). FIG. 16 shows a representation of the chemical structure for this KPV dimer. Dimers can be formed by adding cysteines at the N-termini of any of the above polypeptides and allowing the cysteines of two polypeptides to form a disulfide bond. Both homo-dimers and hetero-dimers can be formed using this method.

Statistical significance disclosed in the examples below was analyzed using one-way analysis of variance and the Student's t test. Probability values greater than 0.05 were considered significant.

EXAMPLE I

This example illustrates the anti-microbial properties of α-MSH and/or its derivatives against *Staphylococcus aureus*.

Cultures of *S. aureus* (ATCC 29213) were obtained from the collection of the Department of Microbiology, Ospedale Maggiore di Milano. *S. aureus* ($1 \times 10^6$/ml in Hank's balanced salt solution) was incubated in the presence or absence of α-MSH (1–13) (SEQ. ID. NO. 4), α-MSH (11–13) (SEQ. ID. NO. 1), or the KPV dimer at concentrations in the range of $10^{-15}$ to $10^{-4}$ M for two hours at 37° C. Cells were then washed in cold distilled water and diluted with HBSS to a concentration of 100 organisms/ml. One-milliliter aliquots were dispensed on blood agar plates and incubated for 24 hours at 37° C. Viability of the microorganisms was estimated from the colonies formed. In another set of experiments, 500 units of urokinase, a *S. aureus* growth enhancer, were also incubated with the bacteria ($10^5$/100 ml) for four hours at 37° C. in a shaking water bath together with the peptides.

Figure 2:
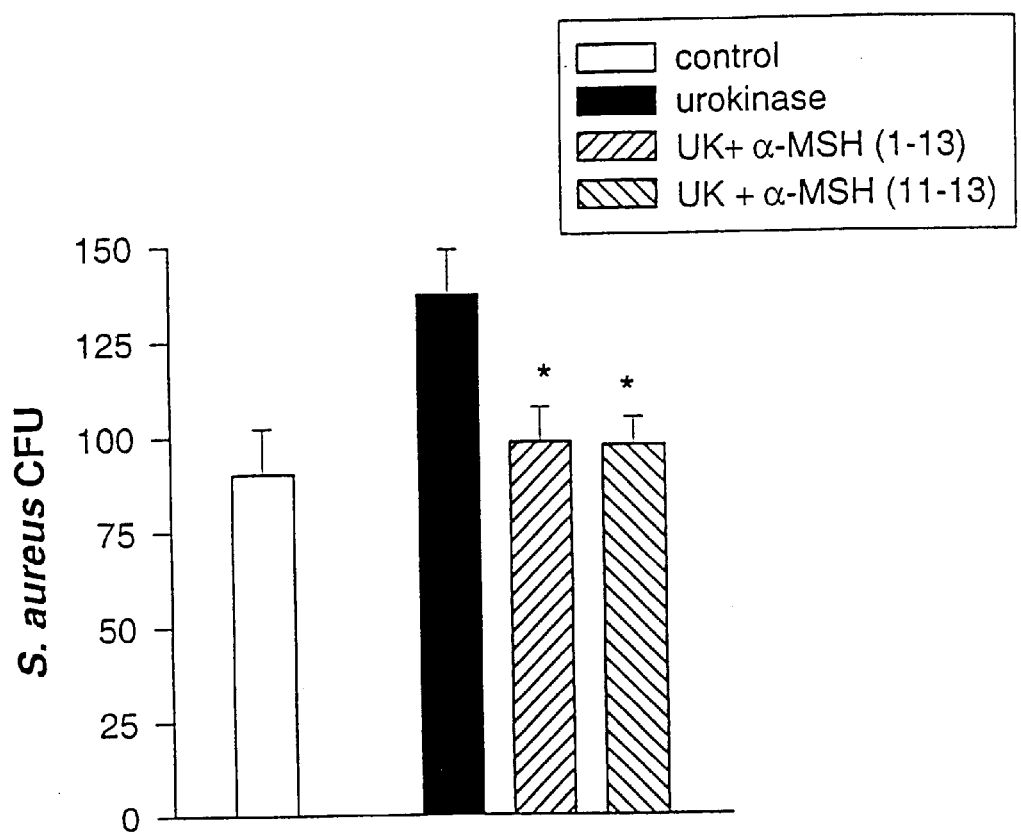
FIG. 2 shows the effects of α-MSH and/or its derivatives on urokinase induced growth of *S. aureus*.

FIG. 1 shows that α-MSH (1–13) (SEQ. ID. NO. 4), α-MSH (11–13) (SEQ. ID. NO. 1), and the KPV dimer all inhibited *S. aureus* colony formation. These inhibitory effects occurred over a wide range of concentrations and were significant (p>0.01) with peptide concentrations of $10^{-12}$ to $10^{-4}$ M. FIG. 2 shows that α-MSH (1–13) (SEQ. ID. NO. 4) and α-MSH (11–13) (SEQ. ID. NO. 1) at concentrations of $10^{-6}$ M significantly countered the growth enhancing effect of urokinase. Thus, α-MSH or its derivatives can inhibit the growth of *Staphylococcus aureus*, an agent known to cause toxic shock syndrome associated with tampon use, vaginitis, UTIs, urethritis, and balanoposthitis.

EXAMPLE II

This example illustrates the anti-fungal properties of α-MSH and/or its derivatives against *Candida albicans*.

Clinical isolates of *C. albicans* were also obtained from the collection of the Department of Microbiology, Ospedale Maggiore di Milano. Cultures of *C. albicans* were maintained on Sabouraud's agar slants and periodically transferred to Sabouraud's agar plates and incubated for 48 hours at 28° C. To prepare stationary growth-phase yeast, a colony was taken from the agar plate, transferred into 30 ml of Sabouraud-dextrose broth, and incubated for 72 hours at 32° C. Cells were centrifuged at 1000×g for ten minutes, and the pellet was washed twice with distilled water. Cells were counted and suspended in Hank's balanced salt solution ("HBSS") to the desired concentration. Viability, determined by exclusion of 0.01% methylene blue, remained greater than 98%.

At $1\times10^6$/ml in HBSS, these fungi were incubated in the presence or absence of α-MSH (1–13) (SEQ. ID. NO. 4), α-MSH (11–13) (SEQ. ID. NO. 1), or the KPV dimer at concentrations ranging from $10^{-15}$ to $10^{-4}$ M for two hours at 37° C. Cells were then washed in cold distilled water and diluted with HBSS to a concentration of 100 organisms/ml. One-milliliter aliquots were then dispensed on blood agar plates and incubated for 48 hours at 37° C. The organism's viability was estimated from the number of colonies formed.

Figure 3:
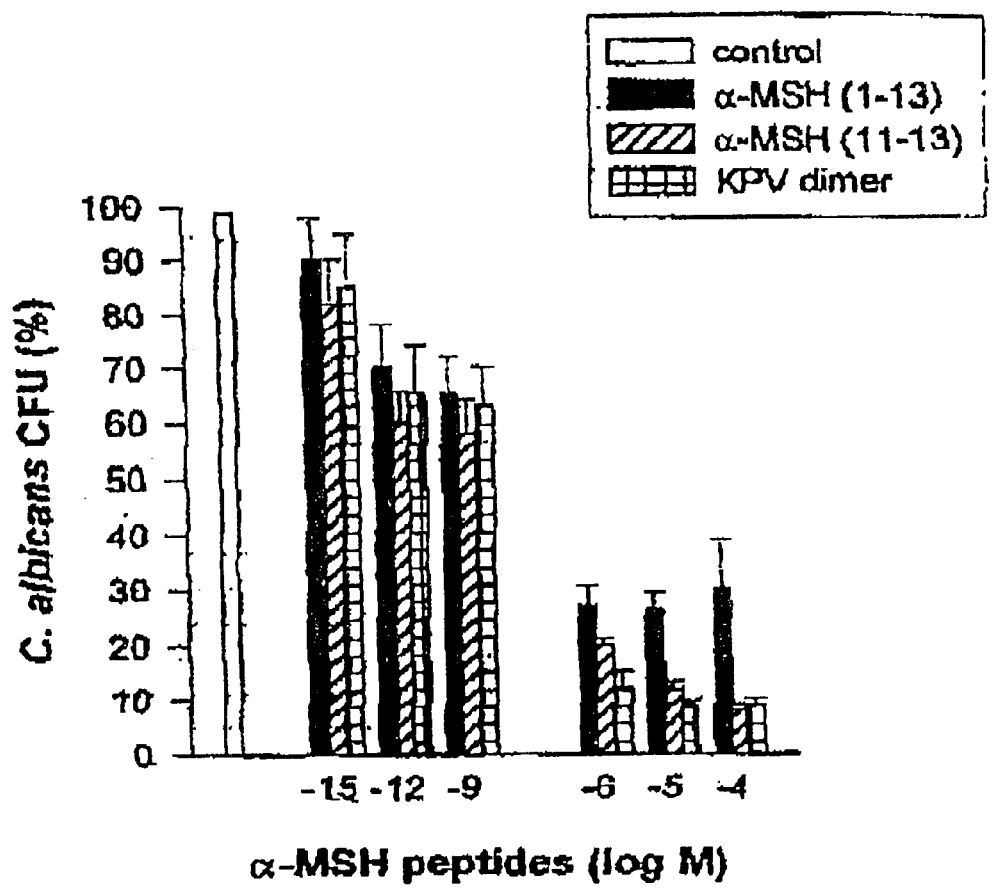
FIG. 3 shows the inhibitory effects of α-MSH and/or its derivatives on the growth of *C. albicans*.

FIG. 3 shows that α-MSH(1–13) (SEQ. ID. NO. 4), α-MSH(11–13) (SEQ. ID. NO. 1), and the KPV dimer greatly reduced the ability of *C albicans* to form colony at concentrations ranging from $10^{-12}$ to $10^{-4}$ M ($p<0.01$ vs. control). Thus, this demonstrates that α-MSH or its derivatives can inhibit the growth of *Candida albicans*, an agent known to cause candidiasis, vaginitis, urethritis, and balanoposthitis.

EXAMPLE III

Figure 4:
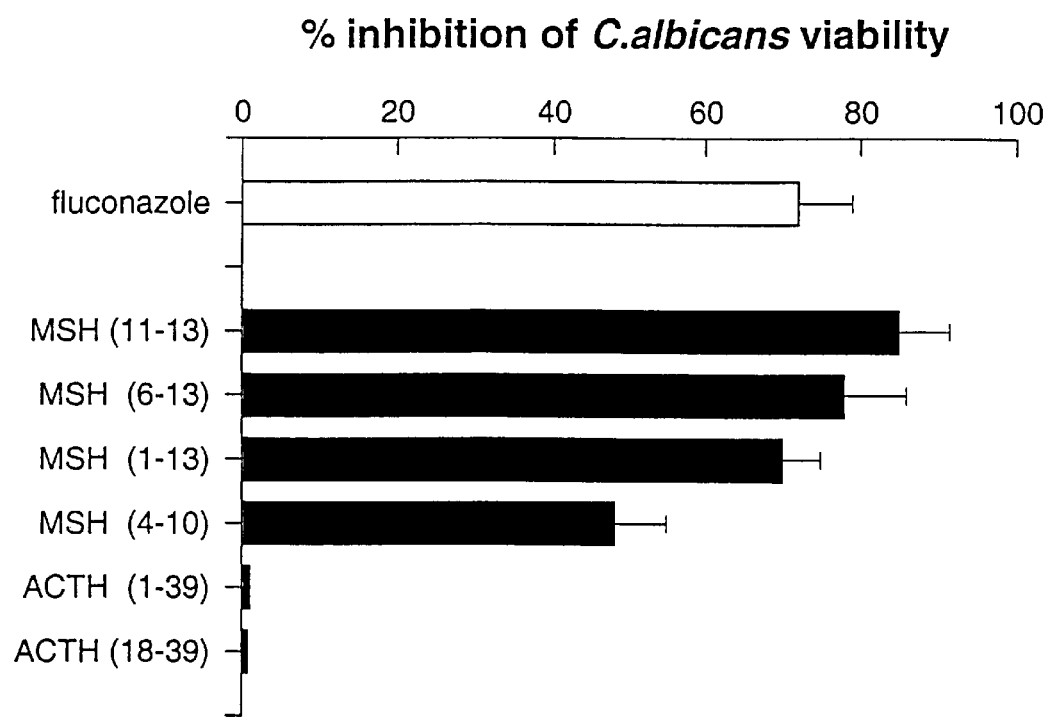
FIG. 4 compares the anti-fungal activities of α-MSH and/or its derivatives with fluconazole.
Figure 5:
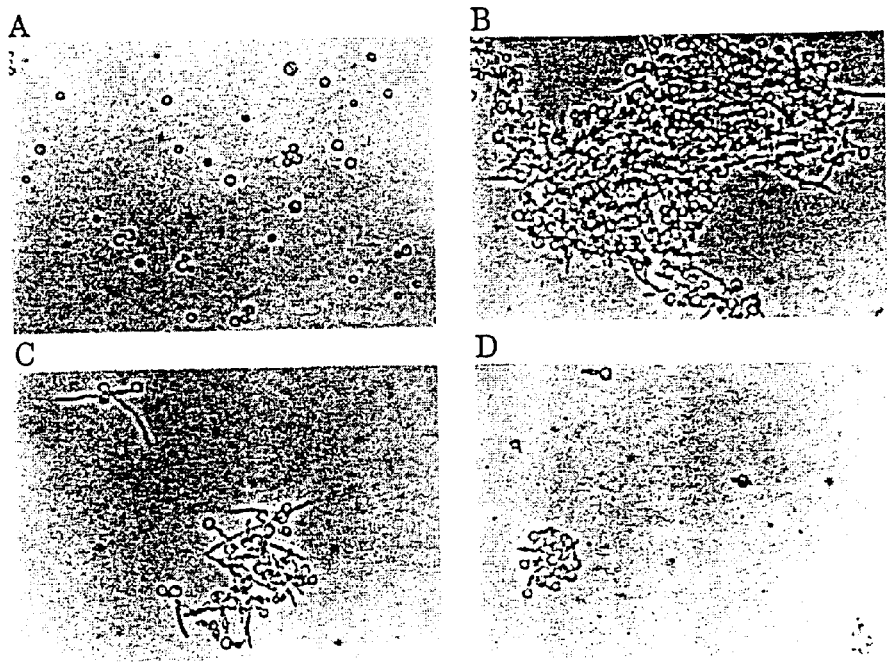
FIGS. 5A to 5D show the inhibitory effects of α-MSH and/or its derivatives on *C. albicans*' germ tube formation.

This example compares the anti-infection activities of α-MSH and/or its derivatives to fluconazole, an established anti-fungal agent.

α-MSH (1–13) (SEQ. ID. NO. 4), (4–10) (SEQ. ID. NO. 2), (6–13) (SEQ. ID. NO. 3), (11–13) (SEQ. ID. NO.1), ACTH (1–39), (18–39), and fluconazole, at concentrations of $10^{-6}$ to $10^{-4}$ M, were tested against *C. albicans* using the same procedures as in Example II. FIG. 4 shows that compared with fluconazole, α-MSH (11–13) (SEQ. ID. NO. 1), (6–13) (SEQ. ID. NO. 3), and (1–13) (SEQ. ID. NO. 4) were most effective against *C. albicans*. Their inhibitory activities were similar to fluconazole at the same molar concentration. In contrast, the "core" α-MSH sequence (4–10) (SEQ. ID. NO. 2), which has behavioral effects but little anti-inflammatory activity, caused approximately 50% inhibition of colony forming units (CFU). Although this inhibitory effect was substantial ($p<0.01$ vs. control), it was significantly less potent that α-MSH fragments bearing the KPV signal sequence, i.e. α-MSH (6–13) (SEQ. ID. NO. 3) and (11–13) (SEQ. ID. NO. 1) ($p<0.01$), or the parent molecule α-MSH (1–13) ($p<0.05$). FIG. 4 also shows that ACTH (1–39) and the ACTH fragment (18–39) did not reduce *C. albicans* viability. Even at a higher concentration of $10^{-4}$ M, which is not shown in the figures, ACTH peptides were likewise ineffective.

Thus, this example demonstrates that α-MSH or its derivatives are as effective as fluconazole in inhibiting Candida's growth.

EXAMPLE IV

This example illustrates that α-MSH and its derivatives inhibit the germination or germ tube formation of *C. albicans*. Germ tube formation is a significant part of the pathogenesis of *C. albicans* infection. This pathogenesis involves adhesion to host epithelial and endothelial cells and morphologic switching from the ellipsoid blastospore to various filamentous forms, e.g. germ tubes, pseudohyphae, and hyphae. Gow, N. A., *Germ Tube Growth of Candida albicans*, Curr. Topics Med. Myco. 8, 43–55 (1997).

*C. albicans* from stationary phase cultures were washed twice with distilled water and suspended in HBSS to a final concentration of $2\times10^6$/ml. Hyphal growth was induced by addition of 10% inactivated horse serum (GIBCO/BRL, Paisley, Great Britain) to yeast incubated for 45 minutes at 37° C. with continuous shaking. Horse serum was then removed by washing cells twice with HBSS, and incubation was further continued for 60 minutes at 37° C. in the presence of α-MSH (1–13) (SEQ. ID. NO. 4), (6–13) (SEQ. ID. NO. 3), or (11–13) (SEQ. ID NO. 1) at a concentration of $10^{-6}$ M with continuous shaking. The percentage of filamentous cells was evaluated under a light microscope with the aid of a hemocytometer. Experiments were run in triplicates and at least 200 cells were scored. Photomicrographs were taken with a MC100 camera attached to an Axioskop Zeiss microscope.

FIG. 5A to 5D show that co-incubation of *C. albicans* with α-MSH (1–13) (SEQ. ID. NO. 4) or (11–13) (SEQ. ID. NO. 1)inhibited germ tube formation induced by horse serum. α-MSH (1–13) (SEQ. ID. NO. 4) caused 28–32% reduction in the number of filamentous cells while α-MSH (11–13) (SEQ. ID. NO. 1)caused 54–58% reduction. Although not shown in the figures, α-MSH (6–13) (SEQ. ID. NO. 3)similarly had approximately 50% reduction in the number of filamentous cells. Thus, this demonstrates α-MSH or its derivatives can inhibit one mode of Candida pathogenesis by inhibiting its germ tube formation.

EXAMPLE V

Reduced killing of pathogens is a dire consequence of therapy with corticosteriods and other nonsteriodal anti-inflanimatory drugs during infection. Stevens, D. L., *Could Nonsteriodal Anti-inflammatory Drugs (NSAIDs) Enhance Progression of Bacterial Infections to Toxic Shock Syndrome?*, Clin. Infect. Dis. 21, 977–80 (1997); Capsoni, F., et. al., *Effect of Corticosteriods on Neutrophil Function: Inhibition of Antibody-dependent Cell-Mediated Cytotoxicity (ADCC)*, J. Immunopharmacol. 5, 217–30 (1983). This example illustrates that α-MSH and/or its derivatives inhibit the growth of infectious agents without comprising the ability of human neutrophils to combat these infections. This example further shows that α-MSH or its derivatives can actually enhance the ability of neutrophils to kill these infectious agents.

Venous blood (20 ml) from healthy volunteers was anticoagulated with heparin. Neutrophils were then isolated using dextran sedimentation and centrifugation with Ficoll-Hypaque (Sigma Chemical Co., St. Louis, Mo. USA). Erythrocytes were lysed via hypotonic shock with the resulting neutrophils representing at least 97% of the cell suspension. Cell viability, estimated by trypan blue exclusion, was greater than 98%. Neutrophils were resuspended in HBSS for the experiments.

*C. albicans* ($1\times10^6$) were opsonized with human AB serum in a shaking water bath for 30 minutes at 37° C. They were then incubated with neutrophils in the presence of medium alone, or medium with α-MSH (1–13) (SEQ. ID. NO. 4)or α-MSH (11–13) (SEQ. ID. NO. 1) in concentrations ranging from $10^{-15}$ to $10^{-4}$ M in a shaking water bath for two hours at 37° C. After incubation, the culture tubes were placed on ice to stop growth, and extracellular organisms were washed twice with centrifugation at 1000-xg at 4° C. A 2.5% sodium deoxycholate solution was added to the suspension, and the tubes were shaken for five minutes. Cold distilled water was then added to obtain a suspension of $10^6$ cells/ml. Two 1/100 serial dilution in HBSS were made to obtain a final suspension of 100 cells/ml. One-milliliter aliquots were then dispensed on blood agar plates and incubated for 48 hours at 37° C. Colony forming units were counted at the end of the incubation period with experiments running in triplicates and repeated using blood from five different donors.

Figure 6:
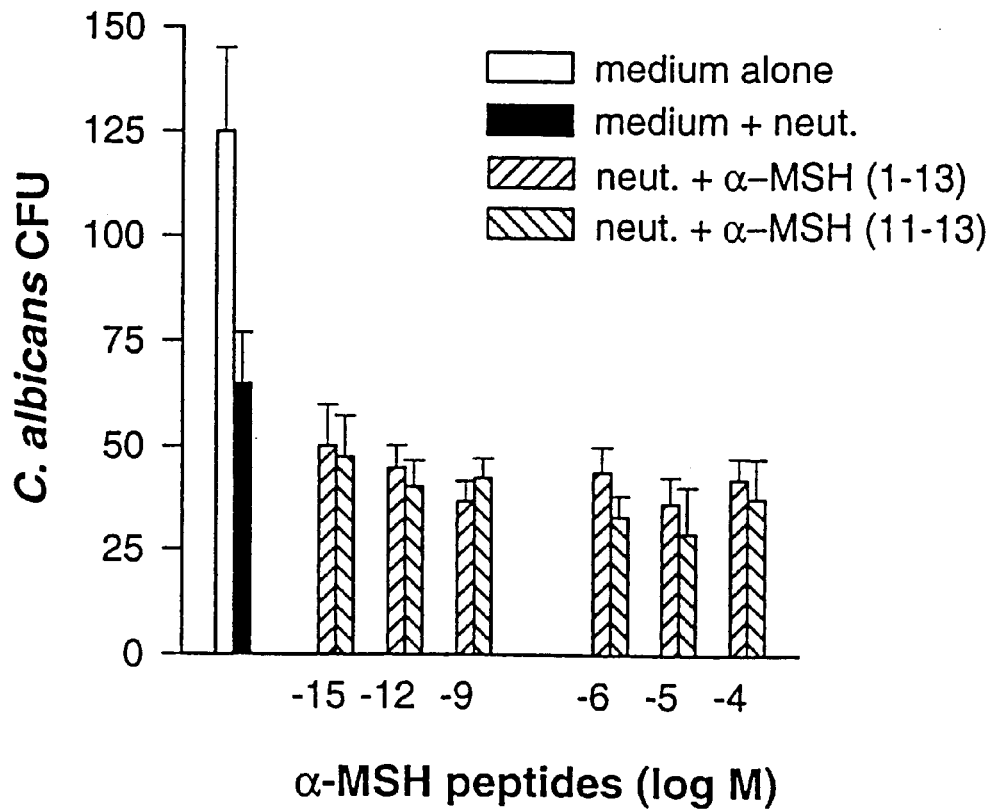
FIG. 6 shows the enhanced neutrophil-killing effects of α-MSH and/or its derivatives against *C. albicans*.

FIG. 6 shows that α-MSH (1–13) (SEQ. ID. NO. 4) and (11–13) (SEQ. ID. NO. 1) actually enhanced neutrophil killing of C. albicans when administered at concentrations ranging from $10^{-12}$ to $10^{-4}$ M ($p<0.01$). It shows that this enhanced killing occurred over a very broad concentration range including picomolar concentration, which is equal to the concentration of α-MSH found in human plasma.

Thus, this example demonstrates that α-MSH or its derivatives can simultaneously combat against infection and inflammation, which may also be applied to candidiasis, vaginitis, urethritis, balanoposthitis, or hemorrhoids.

EXAMPLE VI

This example suggests the cellular mechanism by which α-MSH and/or its derivatives exerts its anti-microbial properties in general, and anti-fungal properties in particular.

C. albicans ($10^6$/ml), permeabilized with toluene/ethanol, were incubated at 37° C. with continuous shaking in the presence or absence of $10^{-6}$ M α-MSH (1–13) (SEQ. ID. NO. 4), (11–13) (SEQ. ID. NO. 1), or forskolin, an agent known to increase intracellular cAMP. The reactions were stopped after:three minutes by the addition of ice cold ethanol. cAMP levels were measured in duplicates using a commercial enzyme immunoassay kit (Amersham, United Kingdom) after extraction via the liquid-phase method according to the manufacturer's instructions. In a related experiment, C. albicans were also exposed to dideoxyadenosine (ddAdo, Sigma), a potent inhibitor of adenylyl cyclase, at concentrations of 25, 50, and $100\times10^{-5}$ M for two hours and to α-MSH or its derivatives for two additional hours. The effects of forskolin and ddAdo on the ability of C. albicans to form colonies were determined according to the procedures described in Example II.

Figure 7:
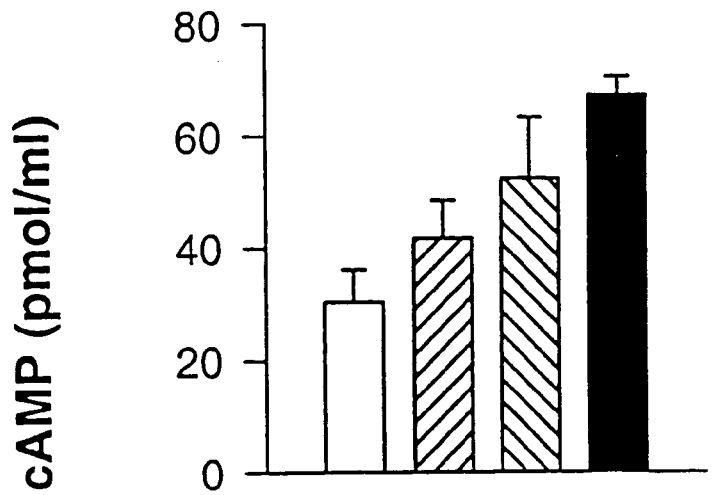
FIG. 7, 8, and 9 show the mechanism by which α-MSH and/or its derivatives inhibit the growth of *C. albicans*.
Figure 8:
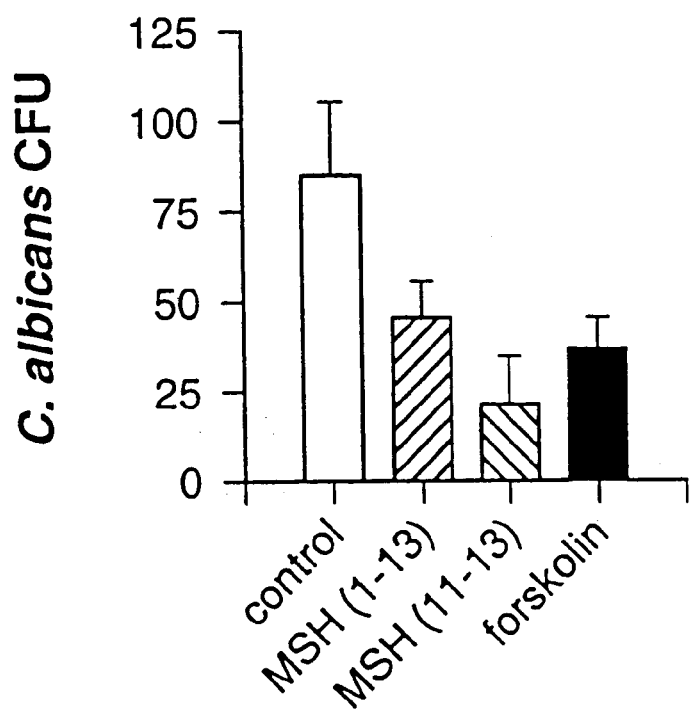
Figure 9:
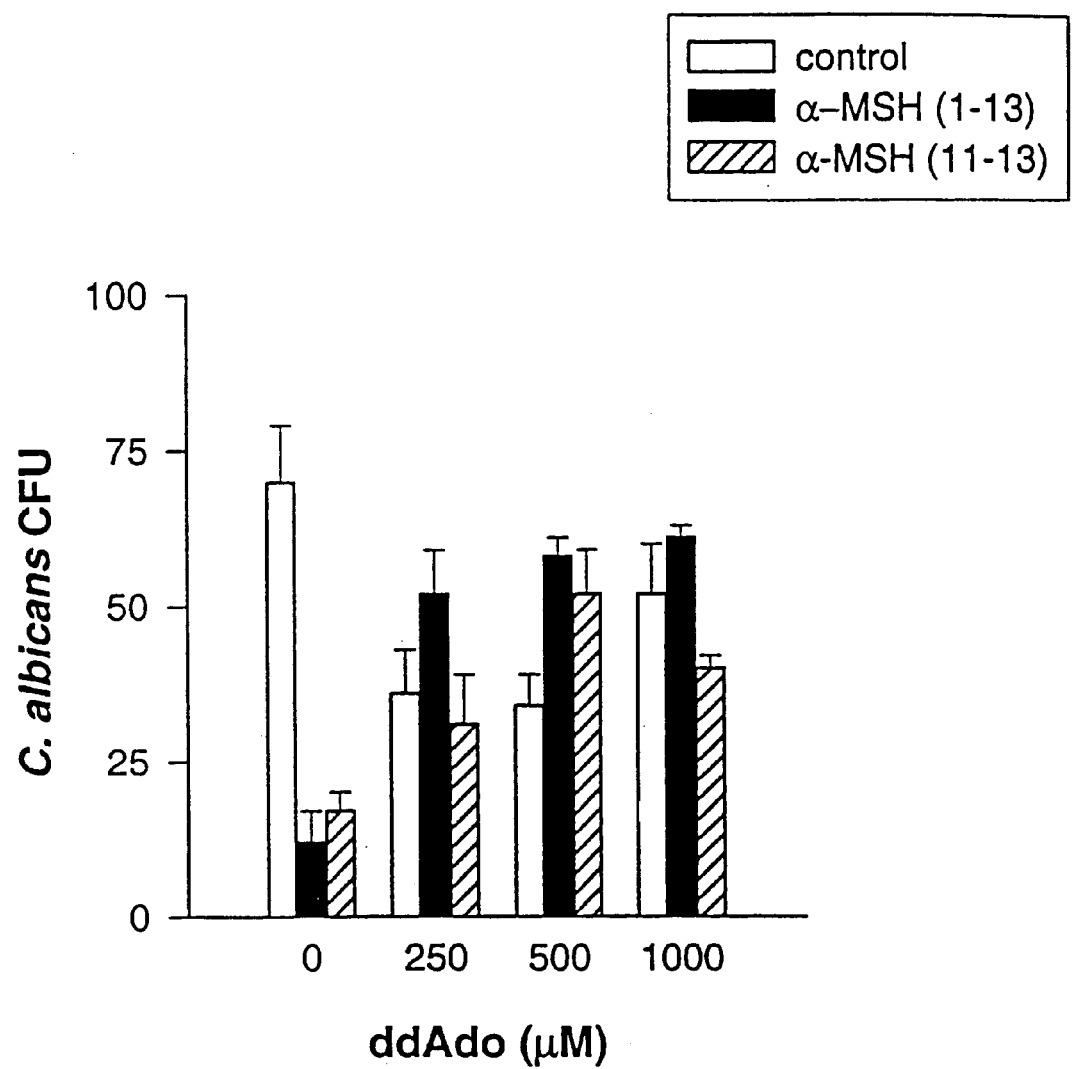

FIG. 7 shows that α-MSH (1–13) (SEQ. ID. NO. 4) and (11–13) (SEQ. ID. NO. 1) enhanced cAMP content in the C. albicans. This cAMP increase was of the same order of magnitude as that induced by equimolar forskolin. FIG. 8 shows that along with α-MSH (1–13) (SEQ. ID. NO. 4) and (11–13) (SEQ. ID. NO. 1), forskolin also significantly inhibited the growth of C. albicans relative to control ($p<0.01$). FIG. 9 shows that ddAdo has the ability to reverse the effect of α-MSH (1–13) (SEQ. ID. NO. 4) and (11–13) (SEQ. ID. NO. 1) on the growth of C. albicans.

This example demonstrates that α-MSH and its derivatives most likely inhibit growth of C. albicans and other microorganisms by increasing its cAMP level, which in turn inhibits mRNA and protein synthesis. see e.g. Bhattacharya A., et. al., *Effect of Cyclic AMP on RNA and Protein Synthesis in Candida albicans, Biochem, Biophysics. Res. Commun.*, 77: 1483–44 (1977).

EXAMPLE VII

This example illustrates the ability of α-MSH or its derivatives to inhibit viral replication in human cells. More specifically, α-MSH inhibited the replication and expression of HIV-1 in chronically infected human monocytes.

Chronically HIV-1 infected promonocytic U1 cell line is an in vitro model of latent HIV infection in monocytes. These cells carry two integrated proviral copies of HIV, and constitutive expression of HIV is very low. Viral replication, however, as measured by RNA transcription, p24 antigen, or reverse transcriptase release, can be activated with different stimuli such as TNF-α, IL-6, IL-10, PMA or crowding of cells.

To determine the effects of α-MSH and/or its derivatives on HIV replication, these cells were maintained in log phase of growth in complete culture medium (RPMI 1640 supplemented with 10 mM Hepes), 2 mM L-glutamine (Sigma-Aldrich), 10% heat-inactivated FCS (Hyclone Laboratories, Logan, Utah, USA), penicillin at 100 units/ml and streptomycin at 100 µg/ml (Gibco Laboratories, Grand Island, N.Y.) in log phase of growth. Pilot experiments were first performed to determine optimal cell density, stimuli concentration, and kinetics of HIV-1 p24 antigen production using these culture conditions. Before use, cells were washed three times with HBSS to remove extracellular viruses. Cells were then plated onto 24-well flat-bottomed plates at a concentration of $2\times10^5$/ml (final volume of one ml) with medium alone or plus TNF-α(10 ng/ml) (R&D Systems, Oxford, England, UK) in the presence or absence of α-MSH (1–13) (SEQ. ID. NO. 4) or (11–13) (SEQ. ID. NO. 1) in concentrations from $10^{-15}$ to $10^{-4}$ M.

In further experiments, α-MSH (11–13) (SEQ. ID. NO. 1) alone at 10–5 M was added to U1 cells stimulated with TNF-α (10 ng/ml), IL-6 (20ng/ml), IL-10 (20ng/ml) (R&D Systems, Oxford, England, UK), PMA (1 ng/ml) (Sigma-Aldrich), or in crowding conditions. Crowding was achieved by seeding U1 cells at a density of $2\times10^5$/ml and maintaining them in culture at 37° C. in 5% $CO_2$ without changing media for seven days. Cultures activated with cytokines or PMA were maintained for only 48 hours. Supernatants were then removed by centrifugation and assayed for p24 antigen using commercially available ELISA kits from Cellular Products, Inc. in Buffalo, N.Y., USA. Reverse transcriptase releases were also measured using a commercially available kit, ELISA Retrosys RT assay from Innovagen, Lund, Sweden. For these experiments, addition of α-MSH (11–13) (SEQ. ID. NO. 1)occurred on day one, and each condition was tested in triplicates.

Figure 10:
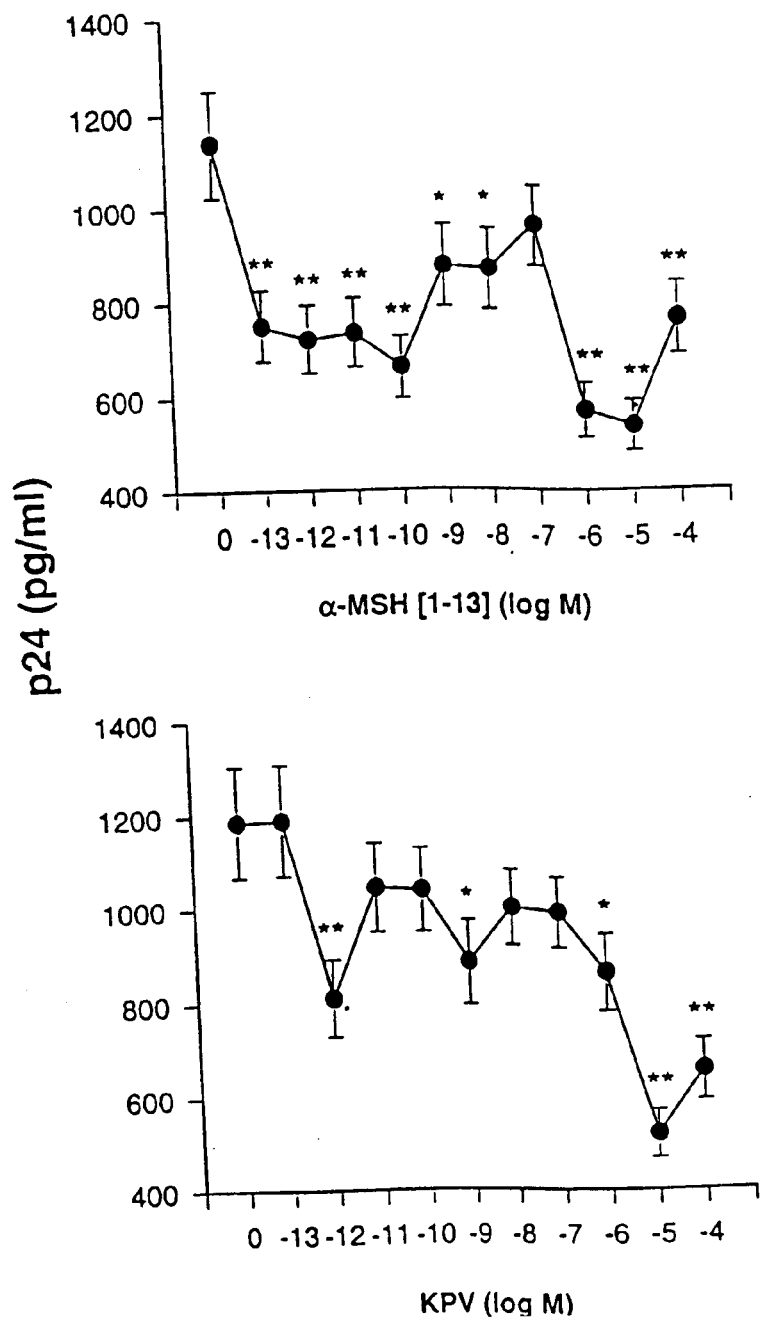
FIG. 10–13 show the inhibitory effects of α-MSH and/or its derivatives on viral replication, expression in chronically infected cells.
Figure 11:
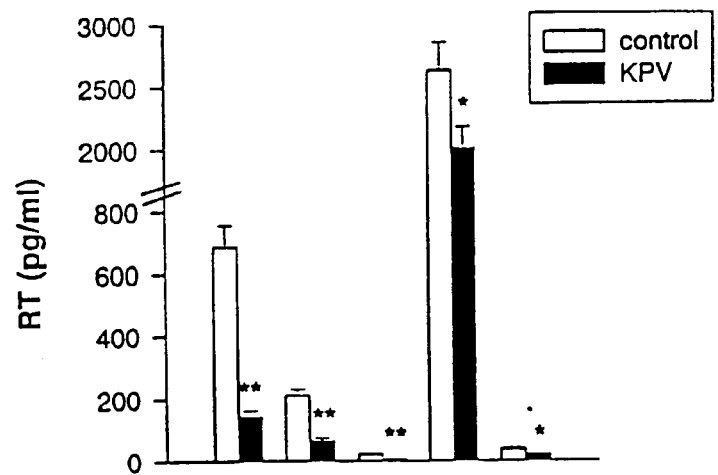
Figure 11:
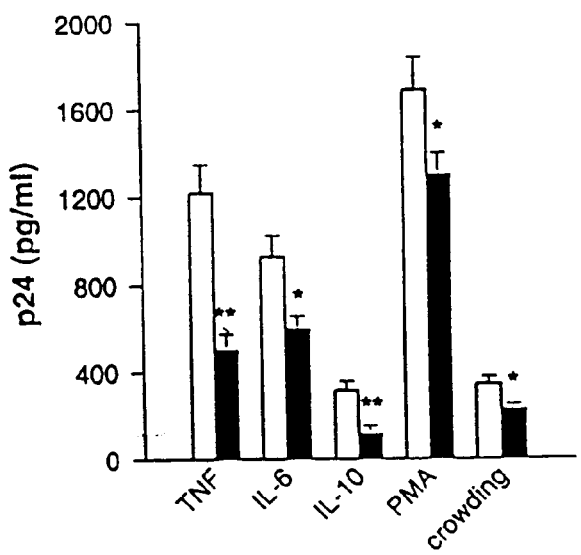
Figure 12:
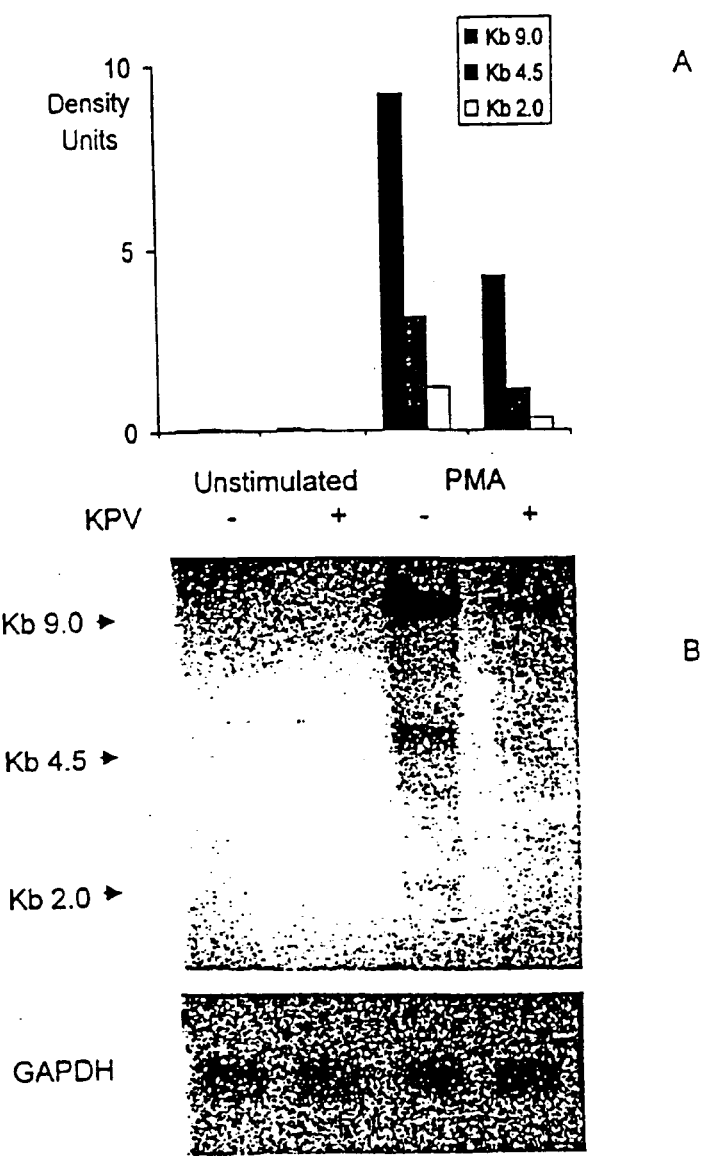

FIG. 10 shows that α-MSH (1–13) (SEQ. ID. NO. [4]) and (11–13) (SEQ. ID. NO. 1) significantly inhibited p24 antigen release from TNF-α stimulated U1 cells over a broad range of concentrations. The most effective concentration for both peptides was $10^{-5}$M, causing 52.7% and 56.0% inhibition respectively. FIG. 11 shows that α-MSH (11–13) (SEQ. ID. NO. 1) also inhibited p24 antigen and reverse transcriptase release from U1 cells induced by IL-6, IL-10, PMA and in crowding condition. In addition, FIG. 12 shows that α-MSH (11–13) (SEQ. ID. NO. 1) also inhibited the transcription of both spliced and unspliced HIV-1 RNA in PMA stimulated U1 cells as measured by Northern Blot analysis.

Thus, this example demonstrates that α-MSH or its derivatives can inhibit transcription of viral genes through mediation of the TNF-α, IL-6, and IL-10 pathways.

EXAMPLE VIII

This example further: illustrates the ability of α-MSH to inhibit viral replication and activation. More specifically, the addition of a neutralizing antibody to α-MSH in U1 cells substantially increased p24-antigen release.

U1 cells were cultured similarly as described in Example VII. Endogenous α-MSH produced by U1 cells was blocked with an affinity purified rabbit-anti-α-MSH antibody (Euro-Diagnostica, Malmo, Sweden) diluted 1:250 with medium. Control antibody was a rabbit IgG at the same dilution. Cells ($2\times10^5$/ml) treated with the anti-α-MSH or the control antibody was coincubated with medium or PMA (1ng/ml). After 48-hour incubation at 37° C., supernatants were separated and tested for p24 antigen release. In crowding experiments with U1 cells cultured as described above, the anti-α-MSH antibody or the control IgG was added on day one and the supernatants were harvested on day seven.

Figure 13:
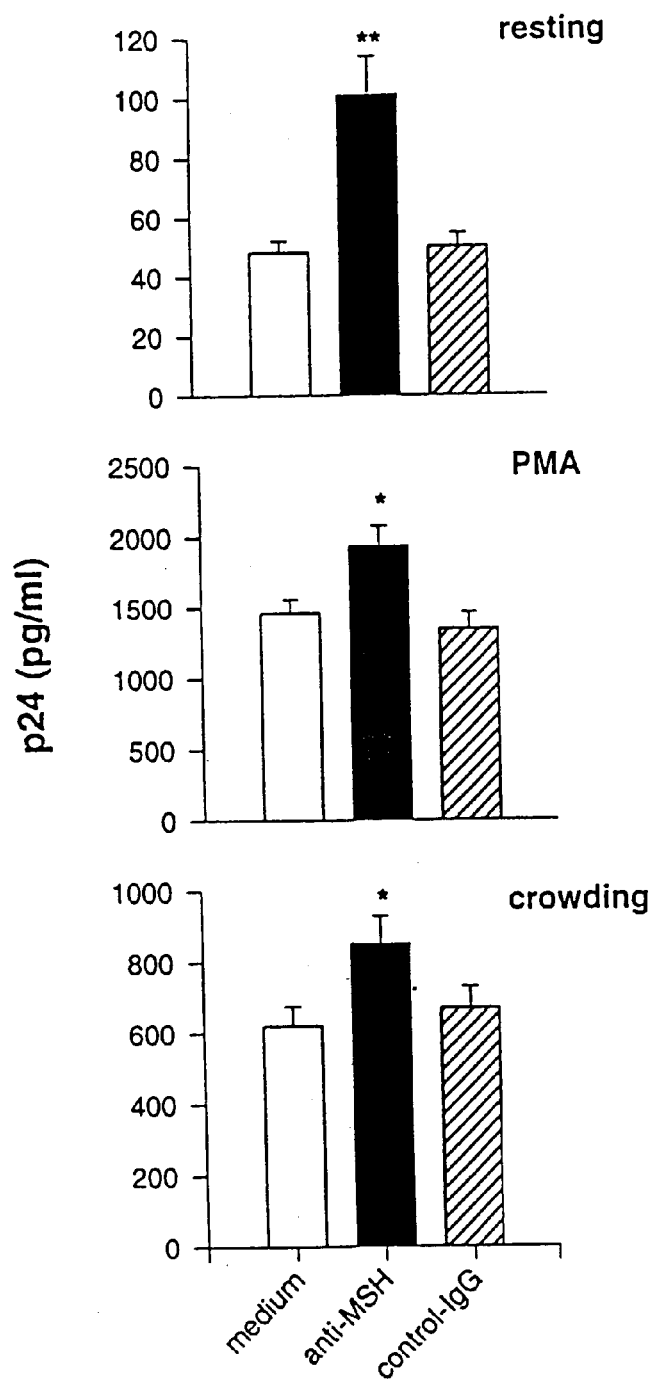

FIG. 13 shows that blocking α-MSH in resting, PMA induced, or crowded U1 cells significantly increased the release of p24 antigen. This example strongly implies that viral replication is affected by α-MSH.

EXAMPLE IX

This example illustrates the mechanism by which α-MSH and/or its derivatives inhibit viral replication and expression. More specifically, α-MSH or its derivatives inhibited TNF-α induced NF-κB activation and binding.

To determine the level of NF-κB activity, nuclear extracts were prepared from $20\times10^6$ U1 cells ($2\times10^5$/ml in complete medium) stimulated for four hours with TNF-α (20 ng/ml) in the presence or absence of $10^{-5}$ M α-MSH (11–13) (SEQ. ID. NO. 1). Cells were washed once with cold PBS, and twice with buffer A (10 mM Hepes pH 7.9, 1.5 mM $MgCl_2$, 10 mM KCl, 0.5 mM PMSF and 0.5 mM DTT), centrifuged, and incubated for ten minutes on ice in buffer A plus 0.1% NP-40. Afterwards, the supernatants were removed, and the nuclear pellets were resuspended in 15 μl of buffer C (20 mM Hepes pH 7.9, 1.5 mM $MgCl_2$, 0.42 M KCl, 0.2 mM EDTA, 25% glycerol, 0.5 mM PMSF, and 0.5 mM DTT), incubated for 15 minutes on ice, mixed, and then centrifuged. The supernatants were diluted with 75 μl of modified buffer D (20 mM Hepes, pH 7.9, 0.05 mM KCl, 0.2 mM EDTA, 20% glycerol, 0.5 mM PMSF, and 0.5 mM DTT) and stored at −80° C. The binding reaction was carried out for fifteen minutes at room temperature with 10 μg of nuclear extract protein and 0.5 ng of $^{32}$P-labelled NF-κB (30,000 cpm/μl) or AP1 consensus in buffer A (12 mM Tris-HCl pH 7.8, 60 mM KCl, 0.2 mM EDTA, 0.3 mM DTT), plus 10% glycerol, 2 μg/ml bovine serum albumin and 1 μg/ml single stranded . . . DNA (Pharmacia Biotech). The oligonucleotides for NF-κB used in these studies were: +GAT CCA AGG GGA CTT TCC GCT GGG GAC TTT CCA TG (SEQ.ID.NO.9), and −GAT CCA TGG AAA GTC CCC AGC GGA AAG TCC CCT TG (SEQ.ID.NO.10). Each oligonucleotide was annealed to its complementary strand and end-labeled with $^{32}$P-γ-ATP using polynucleotide kinase. . . . For the determination of specific bands, nuclear extracts were first incubated with 100 fold excess unlabeled probe for five minutes, before incubation with a labeled probe. The mixtures were then run on 5% (30:1) acrylamide gel in 1× TBE. The gels were dried and autoradiographed.

Figure 14:
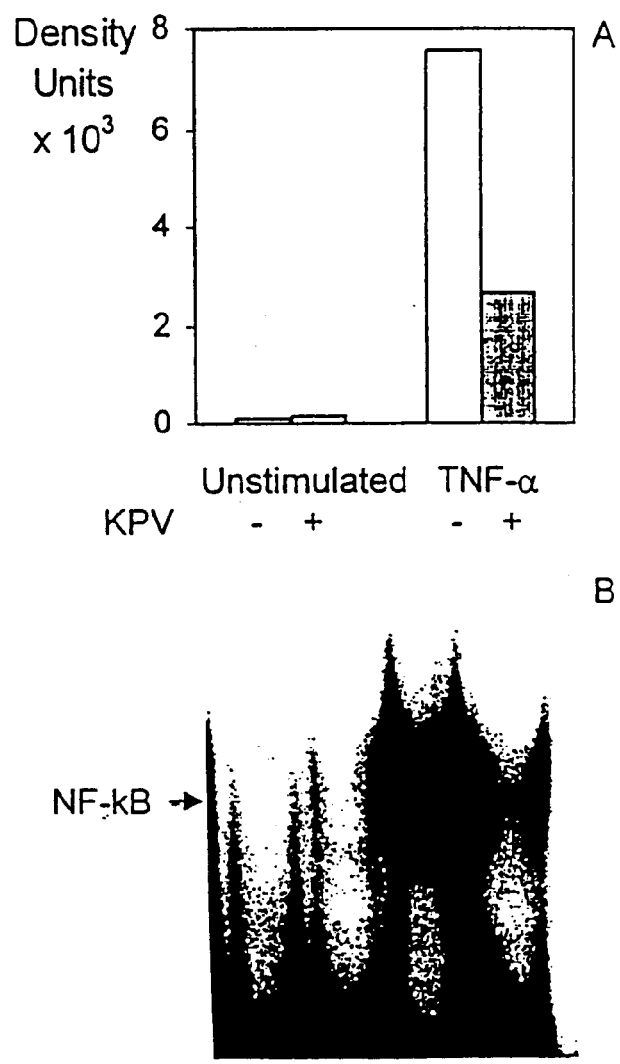
FIG. 14 shows the mechanisms by which α-MSH and/or its derivatives inhibit viral replication, expression, and reactivation.

FIG. 14 shows that TNF-α greatly enhanced NF-κB binding activity, but the co-incubation of α-MSH (11–13) (SEQ. ID. NO. 1) at 10–5 M significantly reduced NF-κB activation. α-MSH (11–13) (SEQ. ID. NO. 1), however, did not alter NF-κB activation in resting cells. This suggests that α-MSH and/or its derivatives inhibit viral replication and expression through regulation of the NF-κB binding.

Replication of viral agents often depends on the state of activation of infected cells and is often regulated by interactions between viral and host factors. These host factors may include TNF-α and other cytokines such as the interleukins. Similar to HIV-1 infection and activation, herpes simplex virus also become reactivated from latency in response to host cytokines. For example, TNF-α and IL-6, but not IL-1 and IL-3, have been shown to reactivate HSV infection. Neutralization of IL-6 with antibody against IL-6 significantly inhibited HSV reactivation while neutralization of interferon alpha and beta did not. see e.g. Baker, M., et. al., *The Relationship between Interleukin-6 and Herpes Simplex Virus Type-1: Implications for Behavior and Imunopathology*, Brain Behav. Immun. 13(3):201–11 (1999); Noisakran S., e. al., *Lymphocytes Delay Kinetics of HSV-1 Reactivation from in vitro Explants of Latent Infected Trigeminal Ganglia*, J. Neuroimmunol. 95(1–2):126–35 (1999); Walev, I., et.al., *Enhancement by TNF-alpha of Reactivation and Replication of Latent Herpes Simplex Virus from Trigeminal Ganglia of Mice*, Arch Virol. 140(6):987–92 (1995); Domk-Optiz, I., et. al., *Stimulation of Macrophages by Endotoxin Results in the Reactivation of a Persistent Herpes Simplex Virus Infection*, Scand J. Immunol. 32(2):69–75 (1990); Fauci, A. S., *Host Factors in the Pathogenesis of HIV-induced Disease*, Nature 384: 529 (1996).

TNF-α or infection by viruses, including HSV, can cause targeted destruction of IκB, which in turn activates the nuclear translocation of NF-κB. Nuclear translocation promotes NF-κB binding to DNA operators for the transcription of a range of inflammatory agents including TNF-α, IL-6, and other cytokines. The expression of these cytokines, again, further reactivates other HSV infected cells to produce HSV viruses. see e.g. Patel, A., et. al., *Herpes Simplex Type 1 Induction of Persistent NF-κB Nuclear Translocation Increases the Efficiency of Virus Replication*, Virology 247 (2):212–22 (1998).

Thus, by blocking NF-κB binding, α-MSH and/or its derivatives inhibit the expression of more inflammatory cytokines that can reactivate HSV. This example and Examples VII-VIII show that α-MSH and/or its derivatives inhibit viral replication, expression, and reactivation by inhibiting NF-κB binding in response to the body's cytokines or other viral infection.

EXAMPLE X

This example illustrates the ability of α-MSH and/or its derivatives to inhibit viral replication in acutely infected human cells. More specifically, α-MSH inhibited the replication and expression of HIV-1 in acutely infected human peripheral blood mononuclear cells (PBMCs).

PBMCs were isolated from normal donors by Ficoll-Hypaque density gradient centrifugation. Monocytes were isolated by Percoll gradient separation and allowed to differentiate into macrophages (MDM) in complete medium of RPMI plus 20% FCS using 24-well tissue culture plates at $10^6$ cells/ml for seven days. MDM were infected with monocytotropic HIVBa-1 strain (1:10) overnight. The undiluted viral stock contained $10^7$ infectious units/ml. After 24 hours, MDM were washed and resuspended in complete medium, replaced three times a week, for three weeks. Reverse transcriptase releases were measured weekly post-infection using a commercially available kit, ELISA Retrosys RT assay from Innovagen, Lund, Sweden. $10^{-5}$ M α-MSH (11–13) (SEQ. ID. NO. 1) was added at the time of HIV infection and daily until harvests.

Figure 15:
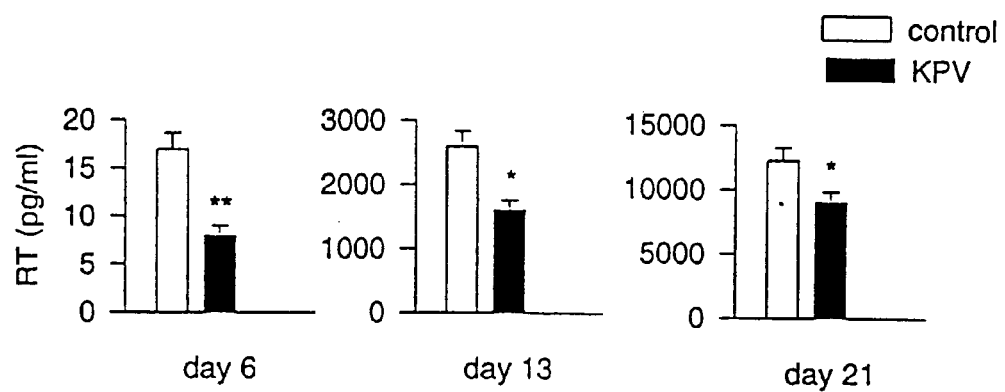
FIG. 15 shows the inhibitory effects of α-MSH and/or its derivatives on viral replication, expression in acutely infected cells.

FIG. 15 shows that α-MSH significantly inhibited reverse transcriptase release in acutely infected MDM. This inhibitory effect was more pronounced on day six but was still statistically significant on day 21.

Thus, this example demonstrates that viral replication at the site of infection can be inhibited by α-MSH or its derivatives. Consequently, the sexual transmission of venereal diseases in general, and HIV in particular can be inhibited by associating α-MSH and/or its derivatives with contraceptives such as condoms, diaphragms, or sponges used during sexual contact, and/or the post sexual contact application of suppositories, cream, ointment, gel, or aerosol foams containing α-MSH and/or its derivatives

EXAMPLE XI

This example illustrates the biological functional equivalents of α-MSH and/or its derivatives.

Although specific amino acid sequences described here are effective, it is clear to those familiar with the art that amino acids can be substituted or deleted without altering the effectiveness of the peptides. Further, it is known that stabilization of the α-MSH sequence can greatly increase the activity of the peptide and that substitution of D-amino acid forms for L-forms can improve or decrease the effectiveness of the peptides. For example, a stable analog of α-MSH, [Nle$^4$,D-Phe$^7$]-α-MSH, which is known to have marked biological activity on melanocytes and melanoma cells, is approximately ten times more potent than the parent peptide in reducing fever. Further, adding amino acids to the C-terminal of α-MSH(11–13) (SEQ. ID. NO. 1) sequence can reduce or enhance antipyretic potency. Addition of glycine to form the 10–13 sequence (SEQ. ID. NO. 5) slightly decreased potency; the 9–13 sequence (SEQ. ID. NO. 6) was almost devoid of activity, whereas the potency of the 8–13 sequence (SEQ. ID. NO. 7) was greater than that of the 11–13 sequence (SEQ. ID. NO. 1). It is known that Ac-[D-K11]-α-MSH 11-13-NH2 has the same general potency as the L-form of the tripeptide α-MSH (11–13) (SEQ. ID. NO. 1). However, substitution with D-proline in position 12 of the tripeptide rendered it inactive. see e.g. Holdeman, M., et. al., *Antipyretic Activity of a Potent α-MSH Analog, Peptides* 6, 273–5 (1985). Deeter, L. B., et. al., *Antipyretic Properties of Centrally Administered α-MSH Fragments in the Rabbit, Peptides* 9, 1285–8 (1989). Hiltz, M. E., *Anti-inflammatory Activity of α-MSH (11–13) Analogs: Influences of Alterations in Stereochemistry, Peptides* 12, 767–71 (1991).

Biological functional equivalents can also be obtained by substitution of amino acids having similar hydropathic values. Thus, for example, isoleucine and leucine, which have a hydropathic index +4.5 and +3.8, respectively, can be substituted for valine, which has a hydropathic index of +4.2, and still obtain a protein having like biological activity. Alternatively, at the other end of the scale, lysine (−3.9) can be substituted for arginine (−4.5), and so on. In general, it is believed that amino acids can be successfully substituted where such amino acid has a hydropathic score of within about +/−1 hydropathic index unit of the replaced amino acid.

Furthermore, these modified analogs of α-MSH and/or its derivatives can also form dimers as exemplified by the KPV dimer in FIG. 16.

EXAMPLE XII

A woman experiences discomfort in her vagina, vulva, and/or urinary tract. An examination by the physician can include a culture be taken from these area. After determining the cause of the discomfort, including any infection or inflammation, the physician may prescribe an antibiotic, anti-fungal, anti-viral, or anti-inflammation drug where appropriate. In addition, the treatment can include a topical application of pharmacologically effective amounts of α-MSH and/or its derivatives carried in an ointment, cream, gel, dissolvable pill, aerosol spray, suppository, liquid solution for douche, or the absorbent material of tampons. The topical treatment can be applied once or multiple times according to the discretion of the physician until the condition is resolved.

This example, where appropriate at the discretion of the physician, can also be applied to a man who experiences discomfort in his penis, testicles, and/or urinary tract. In addition, this topical application of α-MSH and/or its derivatives may also be achieved without a physician such as use as an over the counter drug.

The preceding Examples I–XII demonstrate the anti-infection activities and uses of α-MSH and/or its derivatives. These data are intended only as examples and are not intended to limit the invention to these examples. It is understood that modifying the examples above does not depart from the spirit of the invention. It is further understood that the examples can be applied on its own or in combination with each other.

---

What is claimed is:

1. A composition comprising a dimer wherein the dimer comprises a formula $(Cys-Lys-Pro-Val)_2$.

2. The composition of claim 1 wherein the dimer is a homodimer.

3. The composition of claim 1 wherein the dimer is a heterodimer.

4. The composition of claim 1 wherein at least one amino acid is in the D-form.

5. The composition of claim 1 wherein the dimer is N-acetylated or C-amidated or both.

6. The composition of claim 1 further comprising a carrier.

7. The composition of claim 6 wherein the carrier includes a gel.

8. The composition of claim 6 wherein the carrier is selected from a group consisting of ointment, foam, balm, cream, dissolvable pill, aerosol spray, aerosol foam and liquid solution of a douche.

9. The composition of claim 6 further comprising an applicator.

10. The composition of claim 9 wherein the applicator is selected from the group consisting of syringes, bandages, catheters, and spatulas.

11. A composition comprising a dimer having a formula:

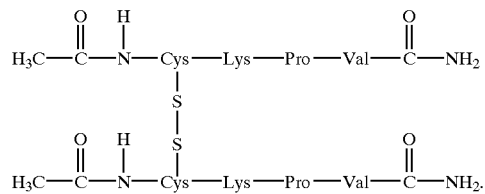

12. The composition of claim 11 wherein at least one amino acid is in the D-form.

13. The composition of claim 11 further comprising a carrier.

14. The composition of claim 13 wherein the carrier includes a gel.

15. The composition of claim 13 wherein the carrier is selected from a group consisting of ointment, foam, balm, cream, dissolvable pill, aerosol spray, aerosol foam and liquid solution of a douche.

16. The composition of claim 13 further comprising an applicator.

17. The composition of claim 16 wherein the applicator is selected from the group consisting of syringes, bandages, catheters, and spatulas.

* * * * *